United States Patent
Preston et al.

(10) Patent No.: US 10,298,735 B2
(45) Date of Patent: May 21, 2019

(54) METHOD AND APPARATUS FOR DYNAMIC CONFIGURATION OF A MULTIPROCESSOR HEALTH DATA SYSTEM

(71) Applicants: Dan Alan Preston, Bainbridge Island, WA (US); Michael Sidney Mason, Gig Harbor, WA (US); Yevgeniy Govorushkin, Tacoma, WA (US); Trinitie Marie Vance, Tahuya, WA (US); Alex Michael Malone, Poulsbo, WA (US); Colin Ross Kreiger, Everett, WA (US); Joseph David Preston, Bainbridge Island, WA (US)

(72) Inventors: Dan Alan Preston, Bainbridge Island, WA (US); Michael Sidney Mason, Gig Harbor, WA (US); Yevgeniy Govorushkin, Tacoma, WA (US); Trinitie Marie Vance, Tahuya, WA (US); Alex Michael Malone, Poulsbo, WA (US); Colin Ross Kreiger, Everett, WA (US); Joseph David Preston, Bainbridge Island, WA (US)

(73) Assignee: NORTHWATER INTELLECTUAL PROPERTY FUND L.P. 2, Toronto (CA)

( * ) Notice: Subject to any disclaimer, the term of this patent is extended or adjusted under 35 U.S.C. 154(b) by 361 days.

(21) Appl. No.: 15/140,950

(22) Filed: Apr. 28, 2016

(65) Prior Publication Data

US 2016/0371450 A1    Dec. 22, 2016

Related U.S. Application Data

(60) Continuation-in-part of application No. 14/981,616, filed on Dec. 28, 2015, now Pat. No. 10,102,013,
(Continued)

(51) Int. Cl.
*G06F 19/00* (2018.01)
*H04M 1/725* (2006.01)
(Continued)

(52) U.S. Cl.
CPC .......... *H04M 1/72522* (2013.01); *G06F 9/46* (2013.01); *G06F 11/2028* (2013.01);
(Continued)

(58) Field of Classification Search
None
See application file for complete search history.

(56) References Cited

U.S. PATENT DOCUMENTS 2,995,318 A    8/1961  Cocharo
3,812,468 A    5/1974  Wollum et al.
(Continued)

FOREIGN PATENT DOCUMENTS

DE    3125161    1/1983
DE    4237987    5/1994
(Continued)

OTHER PUBLICATIONS

A. Das, R. Fierro, V. Kumar, J. Ostrowski, J. Spletzer, and C. Taylor, "A Framework for Vision Based Formation Control", IEEE Transactions on Robotics and Automation, vol. 18, Nov. 5, 2001, pp. 1-13.
(Continued)

*Primary Examiner* — Michael Tomaszewski
(74) *Attorney, Agent, or Firm* — Norton Rose Fulbright Canada LLP; Niall Cooney

(57) ABSTRACT

A health monitoring system which can collect data generated from multiple health, fitness, and environmental data generating devices by a health application running on a portable smart device, or a computing device that is connected to a wireless Bluetooth Network using Secure Simple Pairing.
(Continued)

The generated data is collected by the health application that identifies the device and selectively connects, so that data transfer can be authenticated and securely transmitted.

20 Claims, 30 Drawing Sheets

Related U.S. Application Data which is a continuation of application No. 14/255,435, filed on Apr. 17, 2014, now Pat. No. 9,292,334, which is a continuation of application No. 12/979,198, filed on Dec. 27, 2010, now Pat. No. 8,744,672, which is a division of application No. 12/483,214, filed on Jun. 11, 2009, now Pat. No. 8,958,315, which is a continuation of application No. 11/462,958, filed on Aug. 7, 2006, now Pat. No. 7,778,739, which is a continuation of application No. 09/841,915, filed on Apr. 24, 2001, now Pat. No. 7,146,260.

(60) Provisional application No. 62/154,245, filed on Apr. 29, 2015.

(51) Int. Cl.

| | | |
|---|---|---|
| *G06F 13/40* | (2006.01) | |
| *G06F 9/46* | (2006.01) | |
| *G06F 11/20* | (2006.01) | |
| *G06F 11/30* | (2006.01) | |
| *G06F 11/32* | (2006.01) | |
| *G06Q 30/06* | (2012.01) | |
| *H04L 12/40* | (2006.01) | |
| *H04L 12/403* | (2006.01) | |
| *H04L 29/08* | (2006.01) | |
| *H04L 12/24* | (2006.01) | |
| *H04L 12/46* | (2006.01) | |
| *G06Q 50/22* | (2018.01) | |
| *G16H 40/63* | (2018.01) | |
| *H04W 4/80* | (2018.01) | |

(52) U.S. Cl.
CPC ...... *G06F 11/2035* (2013.01); *G06F 11/2046* (2013.01); *G06F 11/3013* (2013.01); *G06F 11/3051* (2013.01); *G06F 11/328* (2013.01); *G06F 13/4081* (2013.01); *G06F 19/00* (2013.01); *G06Q 30/0641* (2013.01); *G06Q 50/22* (2013.01); *G16H 40/63* (2018.01); *H04L 12/403* (2013.01); *H04L 12/40169* (2013.01); *H04L 12/4625* (2013.01); *H04L 41/00* (2013.01); *H04L 67/12* (2013.01); *H04W 4/80* (2018.02); *H04L 41/0809* (2013.01); *H04L 2012/40273* (2013.01); *Y10T 307/50* (2015.04)

(56) References Cited

U.S. PATENT DOCUMENTS

| | | |
|---|---|---|
| 4,303,978 A | 12/1981 | Shaw |
| 4,528,563 A | 7/1985 | Takeuchi |
| 4,558,460 A | 12/1985 | Tanaka |
| 4,591,976 A | 5/1986 | Webber |
| 4,735,274 A | 4/1988 | Good et al. |
| 4,829,434 A | 5/1989 | Karmel |
| 4,835,537 A | 5/1989 | Manion |
| 4,907,159 A | 3/1990 | Mauge |
| 4,931,930 A | 6/1990 | Shyu et al. |
| 4,959,800 A | 9/1990 | Woolley et al. |
| 4,973,771 A | 11/1990 | Cantrell et al. |
| 5,008,678 A | 4/1991 | Herman |
| 5,027,432 A | 6/1991 | Skala |
| 5,031,330 A | 7/1991 | Stuart |
| 5,045,937 A | 9/1991 | Myrick |
| 5,111,401 A | 5/1992 | Everett, Jr. |
| 5,115,245 A | 5/1992 | Wen |
| 5,243,640 A | 9/1993 | Hadley et al. |
| 5,245,909 A | 9/1993 | Corrigan |
| 5,287,199 A | 2/1994 | Zoccolillo |
| 5,303,297 A | 4/1994 | Hillis |
| 5,339,086 A | 8/1994 | DeLuca |
| 5,341,301 A | 8/1994 | Shirai |
| 5,438,361 A | 8/1995 | Coleman |
| 5,440,726 A | 8/1995 | Fuchs et al. |
| 5,471,214 A | 11/1995 | Faibish |
| 5,485,892 A | 1/1996 | Fujita |
| 5,500,794 A | 3/1996 | Fujita et al. |
| 5,506,963 A | 4/1996 | Ducateau |
| 5,532,706 A | 7/1996 | Reinhardt |
| 5,537,539 A | 7/1996 | Narihiro |
| 5,552,773 A | 9/1996 | Kuhnert |
| 5,555,503 A | 9/1996 | Kyrtsos et al. |
| 5,572,201 A | 11/1996 | Graham |
| 5,579,219 A | 11/1996 | Mori et al. |
| 5,581,462 A | 12/1996 | Rogers |
| 5,585,798 A | 12/1996 | Yoshioka |
| 5,617,085 A | 4/1997 | Tsutsumi |
| 5,646,612 A | 7/1997 | Byon |
| 5,661,811 A | 8/1997 | Huemann et al. |
| 5,742,141 A | 4/1998 | Czekaj |
| 5,749,060 A | 5/1998 | Graf |
| 5,751,211 A | 5/1998 | Shirai |
| 5,754,123 A | 5/1998 | Nashif et al. |
| 5,761,320 A | 6/1998 | Farinelli |
| 5,786,998 A | 7/1998 | Neeson |
| 5,787,246 A | 7/1998 | Lichtman |
| 5,793,366 A | 8/1998 | Mano et al. |
| 5,794,164 A | 8/1998 | Beckert et al. |
| 5,859,878 A | 1/1999 | Phillips et al. |
| 5,872,508 A | 2/1999 | Taoka |
| 5,898,392 A | 4/1999 | Bambini |
| 5,907,293 A | 5/1999 | Tognazzini |
| 5,909,559 A | 6/1999 | So |
| 5,915,214 A | 6/1999 | Reece |
| 5,943,427 A | 8/1999 | Massie |
| 5,948,040 A | 9/1999 | DeLorme et al. |
| 5,951,620 A | 9/1999 | Ahrens et al. |
| 5,956,016 A | 9/1999 | Kuenzner et al. |
| 5,956,025 A | 9/1999 | Goulden et al. |
| 5,956,250 A | 9/1999 | Gudat et al. |
| 5,957,985 A | 9/1999 | Wong |
| 5,959,536 A | 9/1999 | Chambers |
| 5,963,092 A | 10/1999 | VanZalinge |
| 5,964,822 A | 10/1999 | Alland |
| 5,966,658 A | 10/1999 | Kennedy, III |
| 5,969,598 A | 10/1999 | Kimura |
| 5,974,554 A | 10/1999 | Oh |
| 5,977,906 A | 11/1999 | Ameen |
| 5,983,092 A | 11/1999 | Whinnett |
| 5,983,161 A | 11/1999 | Lemelson |
| 6,009,330 A | 12/1999 | Kennedy, III |
| 6,009,403 A | 12/1999 | Sato |
| 6,028,537 A | 2/2000 | Suman |
| 6,028,548 A | 2/2000 | Farmer |
| 6,032,089 A | 2/2000 | Buckely |
| 6,032,202 A | 2/2000 | Lea et al. |
| 6,037,860 A | 3/2000 | Zander et al. |
| 6,038,625 A | 3/2000 | Ogino et al. |
| 6,052,632 A | 4/2000 | Iihoshi |
| 6,054,950 A | 4/2000 | Fontana |
| 6,060,989 A | 5/2000 | Gehlot |
| 6,061,002 A | 5/2000 | Weber et al. |
| 6,061,709 A | 5/2000 | Bronte |
| 6,075,467 A | 6/2000 | Ninagawa |
| 6,097,285 A | 8/2000 | Curtin |
| 6,097,314 A | 8/2000 | Desens et al. |
| 6,105,119 A | 8/2000 | Kerr et al. |
| 6,128,608 A | 10/2000 | Barnhill |
| 6,144,336 A | 11/2000 | Preston et al. |
| 6,148,261 A | 11/2000 | Obradovich |

(56) References Cited

U.S. PATENT DOCUMENTS

| | | |
|---|---|---|
| 6,150,961 A | 11/2000 | Alewine |
| 6,154,123 A | 11/2000 | Kleinberg |
| 6,161,071 A | 12/2000 | Shuman |
| 6,163,711 A | 12/2000 | Juntunen |
| 6,166,627 A | 12/2000 | Reeley |
| 6,167,253 A | 12/2000 | Farris |
| 6,169,894 B1 | 1/2001 | McCormick |
| 6,175,728 B1 | 1/2001 | Mitama |
| 6,175,782 B1 | 1/2001 | Obradovich |
| 6,179,489 B1 | 1/2001 | So et al. |
| 6,181,922 B1 | 1/2001 | Iwai |
| 6,181,994 B1 | 1/2001 | Colson |
| 6,182,006 B1 | 1/2001 | Meek |
| 6,185,491 B1 | 2/2001 | Gray |
| 6,195,760 B1 | 2/2001 | Chung et al. |
| 6,198,996 B1 | 3/2001 | Berstis |
| 6,199,136 B1 | 3/2001 | Shteyn |
| 6,202,027 B1 | 3/2001 | Alland |
| 6,203,366 B1 | 3/2001 | Muller |
| 6,204,804 B1 | 3/2001 | Andersson |
| 6,226,389 B1 | 5/2001 | Lemelson, III |
| 6,233,468 B1 | 5/2001 | Chen |
| 6,236,652 B1 | 5/2001 | Preston |
| 6,240,365 B1 | 5/2001 | Bunn |
| 6,243,450 B1 | 6/2001 | Jansen |
| 6,243,645 B1 | 6/2001 | Moteki et al. |
| 6,243,772 B1 | 6/2001 | Ghori et al. |
| 6,247,079 B1 | 6/2001 | Papa et al. |
| 6,252,544 B1 | 6/2001 | Hoffberg |
| 6,247,144 B1 | 8/2001 | Marcia-Garza |
| 6,275,231 B1 | 8/2001 | Obradovich |
| 6,282,714 B1 | 8/2001 | Ghori et al. |
| D448,366 S | 9/2001 | Youngers |
| 6,292,109 B1 | 9/2001 | Murano |
| 6,292,136 B1 | 9/2001 | Egnell |
| 6,292,747 B1 | 9/2001 | Amro |
| 6,294,987 B1 | 9/2001 | Matsuda |
| 6,295,541 B1 | 9/2001 | Bodnar et al. |
| 6,297,732 B2 | 10/2001 | Hsu |
| 6,298,302 B2 | 10/2001 | Walgers |
| 6,298,370 B1 | 10/2001 | Tang et al. |
| 6,314,326 B1 | 11/2001 | Fuchu |
| 6,321,344 B1 | 11/2001 | Fenchel |
| 6,326,903 B1 | 12/2001 | Gross |
| 6,327,536 B1 | 12/2001 | Tsuji |
| 6,362,730 B2 | 3/2002 | Razavi et al. |
| 6,362,748 B1 | 3/2002 | Huang |
| 6,370,449 B1 | 4/2002 | Razavi et al. |
| 6,374,286 B1 | 4/2002 | Gee |
| 6,377,860 B1 | 4/2002 | Gray |
| 6,382,897 B2 | 5/2002 | Mattio |
| 6,389,340 B1 | 5/2002 | Rayner |
| 6,401,029 B1 | 6/2002 | Kubota |
| 6,405,132 B1 | 6/2002 | Breed |
| 6,408,174 B1 | 6/2002 | Steijer |
| 6,417,782 B1 | 7/2002 | Darnall |
| 6,421,429 B1 | 7/2002 | Merritt |
| 6,429,789 B1 | 8/2002 | Kiridena |
| 6,429,812 B1 | 8/2002 | Hoffberg |
| 6,430,164 B1 | 8/2002 | Jones |
| 6,433,679 B1 | 8/2002 | Schmid |
| 6,434,447 B1 | 8/2002 | Shteyn |
| 6,442,485 B2 | 8/2002 | Evans |
| 6,445,308 B1 | 9/2002 | Koike |
| 6,445,983 B1 | 9/2002 | Dickson et al. |
| 6,449,541 B1 | 9/2002 | Goldberg et al. |
| 6,452,484 B1 | 9/2002 | Drori |
| 6,463,373 B2 | 10/2002 | Suganuma |
| 6,484,080 B2 | 11/2002 | Breed |
| 6,487,717 B1 | 11/2002 | Brunemann et al. |
| 6,489,884 B1 | 12/2002 | Lamberson et al. |
| 6,493,338 B1 | 12/2002 | Preston |
| 6,496,107 B1 | 12/2002 | Himmelstein |
| 6,496,117 B2 | 12/2002 | Gutta |
| 6,496,689 B1 | 12/2002 | Keller |
| 6,498,939 B1 | 12/2002 | Thomas |
| 6,505,100 B1 | 1/2003 | Stuempfle |
| 6,515,595 B1 | 2/2003 | Obradovich |
| 6,522,875 B1 | 2/2003 | Dowling |
| 6,523,696 B1 | 2/2003 | Saito et al. |
| 6,526,335 B1 | 2/2003 | Treyz et al. |
| 6,542,812 B1 | 4/2003 | Obradovich et al. |
| 6,542,814 B2 | 4/2003 | Polidi et al. |
| 6,559,773 B1 | 5/2003 | Berry |
| 6,567,069 B1 | 5/2003 | Bontrager et al. |
| 6,571,136 B1 | 5/2003 | Staiger |
| 6,574,734 B1 | 6/2003 | Colson et al. |
| 6,580,973 B2 | 6/2003 | Leivian et al. |
| 6,584,403 B2 | 6/2003 | Bunn |
| D479,228 S | 9/2003 | Sakaguchi et al. |
| 6,614,349 B1 | 9/2003 | Proctor et al. |
| 6,615,137 B2 | 9/2003 | Lutter |
| 6,616,071 B2 | 9/2003 | Kitamura |
| 6,622,083 B1 | 9/2003 | Knockeart |
| 6,629,033 B2 | 9/2003 | Preston |
| 6,641,087 B1 | 11/2003 | Nelson |
| 6,647,270 B1 | 11/2003 | Himmelstein |
| 6,647,328 B2 | 11/2003 | Walker |
| 6,670,912 B2 | 12/2003 | Honda |
| 6,675,081 B2 | 1/2004 | Shuman |
| 6,678,892 B1 | 1/2004 | Lavelle et al. |
| 6,681,121 B1 | 1/2004 | Preston |
| 6,690,681 B1 | 2/2004 | Preston |
| 6,707,421 B1 | 3/2004 | Drury et al. |
| 6,708,100 B2 | 3/2004 | Russell |
| 6,714,139 B2 | 3/2004 | Saito |
| 6,718,187 B1 | 4/2004 | Takagi et al. |
| 6,725,031 B2 | 4/2004 | Watler |
| 6,734,799 B2 | 5/2004 | Munch |
| 6,738,697 B2 | 5/2004 | Breed |
| 6,748,278 B1 | 6/2004 | Maymudes et al. |
| 6,754,183 B1 | 6/2004 | Razavi et al. |
| 6,756,998 B1 | 6/2004 | Bilger |
| 6,765,495 B1 | 7/2004 | Dunning et al. |
| 6,771,208 B2 | 8/2004 | Lutter |
| 6,771,629 B1 | 8/2004 | Preston |
| 6,778,073 B2 | 8/2004 | Lutter |
| 6,778,924 B2 | 8/2004 | Hanse |
| 6,782,315 B2 | 8/2004 | Lu |
| 6,785,551 B1 | 8/2004 | Richard |
| 6,792,351 B2 | 9/2004 | Lutter |
| 6,799,092 B2 | 9/2004 | Lu |
| 6,801,994 B2 | 10/2004 | Becket et al. |
| 6,806,977 B1 | 10/2004 | Freeny et al. |
| 6,816,458 B1 | 11/2004 | Kroon |
| 6,876,642 B1 | 4/2005 | Adams |
| 6,892,230 B1 | 5/2005 | Gu et al. |
| 6,895,238 B2 | 5/2005 | Newell |
| 6,895,240 B2 | 5/2005 | Laursen |
| 6,901,057 B2 | 5/2005 | Rune |
| 6,906,619 B2 | 6/2005 | Williams |
| 6,917,801 B2 | 7/2005 | Witte et al. |
| 6,920,129 B2 | 7/2005 | Preston |
| 6,925,368 B2 | 8/2005 | Funkhouser et al. |
| 6,937,732 B2 | 8/2005 | Ohmura |
| 6,952,155 B2 | 10/2005 | Himmelstein |
| 6,968,513 B1 | 11/2005 | Rinebold et al. |
| 6,972,669 B2 | 12/2005 | Saito |
| 6,973,030 B2 | 12/2005 | Pecen |
| 6,980,092 B2 | 12/2005 | Turnbull |
| 6,993,511 B2 | 1/2006 | Himmelstein |
| 7,000,469 B2 | 2/2006 | Foxlin |
| 7,006,950 B1 | 2/2006 | Greiffenhagen |
| 7,024,363 B1 | 4/2006 | Comerford |
| 7,039,858 B2 | 5/2006 | Humpleman et al. |
| 7,043,532 B1 | 5/2006 | Humpleman et al. |
| 7,072,945 B1 | 7/2006 | Nieminen et al. |
| 7,079,993 B2 | 7/2006 | Stephenson |
| 7,085,710 B1 | 8/2006 | Beckert et al. |
| 7,089,206 B2 | 8/2006 | Martin |
| 7,092,723 B2 | 8/2006 | Himmelstein |
| 7,103,646 B1 | 9/2006 | Suzuki |
| 7,103,834 B1 | 9/2006 | Humpleman et al. |
| 7,120,129 B2 | 10/2006 | Ayyagari |

(56) References Cited

U.S. PATENT DOCUMENTS

| | | |
|---|---|---|
| 7,123,926 B2 | 10/2006 | Himmelstein |
| 7,146,260 B2 | 12/2006 | Preston |
| 7,151,768 B2 | 12/2006 | Preston |
| 7,158,842 B2 | 1/2007 | Ohmura |
| 7,158,956 B1 | 1/2007 | Himmelstein |
| 7,164,662 B2 | 1/2007 | Preston |
| 7,171,189 B2 | 1/2007 | Bianconi |
| 7,178,049 B2 | 2/2007 | Lutter |
| 7,187,947 B1 | 3/2007 | White |
| 7,206,305 B2 | 4/2007 | Preston |
| 7,207,042 B2 | 4/2007 | Smith |
| 7,215,965 B2 | 5/2007 | Fournier et al. |
| 7,216,347 B1 | 5/2007 | Harrison et al. |
| 7,221,669 B2 | 5/2007 | Preston |
| 7,239,949 B2 | 7/2007 | Lu |
| 7,249,266 B2 | 7/2007 | Margalit |
| 7,257,426 B1 | 8/2007 | Witkowski |
| 7,263,332 B1 | 8/2007 | Nelson |
| 7,264,590 B2 | 9/2007 | Casey |
| 7,269,188 B2 | 9/2007 | Smith |
| 7,272,637 B1 | 9/2007 | Himmelstein |
| 7,274,988 B2 | 9/2007 | Mukaiyama |
| 7,277,693 B2 | 10/2007 | Chen |
| 7,283,567 B2 | 10/2007 | Preston |
| 7,283,904 B2 | 10/2007 | Benjamin |
| 7,286,522 B2 | 10/2007 | Preston |
| 7,289,906 B2 | 10/2007 | van der Merwe et al. |
| 7,317,696 B2 | 1/2008 | Preston |
| 7,337,650 B1 | 3/2008 | Preston |
| 7,343,160 B2 | 3/2008 | Morton |
| 7,375,728 B2 | 5/2008 | Donath |
| 7,379,707 B2 | 5/2008 | DiFonzo |
| 7,411,982 B2 | 8/2008 | Smith |
| 7,418,476 B2 | 8/2008 | Salesky |
| 7,426,437 B2 | 9/2008 | Breed |
| 7,450,955 B2 | 11/2008 | Himmelstein |
| 7,480,501 B2 | 1/2009 | Petite |
| 7,483,964 B1 | 1/2009 | Jackson et al. |
| 7,484,008 B1 | 1/2009 | Gelvin |
| 7,493,645 B1 | 2/2009 | Tranchina |
| 7,506,020 B2 | 3/2009 | Ellis |
| 7,508,810 B2 | 3/2009 | Moinzadeh |
| 7,509,134 B2 | 3/2009 | Fournier et al. |
| 7,536,277 B2 | 5/2009 | Pattipatti et al. |
| 7,579,942 B2 | 8/2009 | Kalik |
| 7,587,102 B2 | 9/2009 | Maris |
| 7,587,370 B2 | 9/2009 | Himmelstein |
| 7,594,000 B2 | 9/2009 | Himmelstein |
| 7,596,391 B2 | 9/2009 | Himmelstein |
| 7,599,715 B2 | 10/2009 | Himmelstein |
| 7,610,331 B1 | 10/2009 | Genske |
| 7,614,055 B2 | 11/2009 | Buskens et al. |
| 7,664,315 B2 | 2/2010 | Woodfill |
| 7,681,448 B1 | 3/2010 | Preston |
| 7,689,321 B2 | 3/2010 | Karlsson |
| 7,689,437 B1 | 3/2010 | Teller et al. |
| 7,733,853 B2 | 6/2010 | Moinzadeh et al. |
| 7,747,281 B2 | 6/2010 | Preston |
| 7,778,739 B2 | 8/2010 | Preston et al. |
| 7,848,763 B2 | 12/2010 | Fournier et al. |
| 7,891,004 B1 | 2/2011 | Gelvin et al. |
| 7,924,934 B2 | 4/2011 | Birmingham |
| 7,928,898 B2 | 4/2011 | Fraenken |
| 7,966,111 B2 | 6/2011 | Moinzadeh et al. |
| 7,970,500 B2 | 6/2011 | Parra Carque |
| 7,979,095 B2 | 7/2011 | Birmingham |
| 7,983,310 B2 | 7/2011 | Hirano et al. |
| 8,014,942 B2 | 9/2011 | Moinzadeh et al. |
| 8,036,201 B2 | 10/2011 | Moinzadeh et al. |
| 8,036,600 B2 | 10/2011 | Garrett et al. |
| 8,045,729 B2 | 10/2011 | Preston et al. |
| 8,063,347 B1 | 11/2011 | Urbano et al. |
| 8,068,792 B2 | 11/2011 | Preston et al. |
| 8,073,707 B2 | 12/2011 | Teller et al. |
| 8,108,092 B2 | 1/2012 | Phillips et al. |
| 8,165,057 B2 | 4/2012 | Preston et al. |
| 8,204,927 B1 | 6/2012 | Duong et al. |
| 8,244,408 B2 | 8/2012 | Lee et al. |
| 8,255,697 B2 | 8/2012 | Mathiessen |
| 8,260,515 B2 | 9/2012 | Huang et al. |
| 8,331,279 B2 | 12/2012 | Preston et al. |
| 8,346,186 B1 | 1/2013 | Preston et al. |
| 8,382,590 B2 | 2/2013 | Stivoric et al. |
| 8,398,546 B2 | 3/2013 | Pacione et al. |
| 8,583,263 B2 | 11/2013 | Hoffberg et al. |
| 8,751,712 B2 | 6/2014 | Preston et al. |
| 8,761,821 B2 | 6/2014 | Tibbitts |
| 8,762,610 B2 | 6/2014 | Preston |
| 8,958,315 B2 | 2/2015 | Preston et al. |
| 8,963,736 B2 | 2/2015 | Millar |
| 9,595,660 B2 | 3/2017 | Akiyama et al. |
| 2001/0009855 A1 | 7/2001 | L'Anson |
| 2002/0012329 A1 | 1/2002 | Atkinson |
| 2002/0017567 A1 | 2/2002 | Connolly et al. |
| 2002/0022927 A1 | 2/2002 | Lemelson et al. |
| 2002/0070852 A1 | 6/2002 | Trauner |
| 2002/0083143 A1 | 6/2002 | Cheng |
| 2002/0085043 A1 | 7/2002 | Ribak |
| 2002/0095501 A1 | 7/2002 | Chiloyan et al. |
| 2002/0098878 A1 | 7/2002 | Mooney et al. |
| 2002/0105423 A1 | 8/2002 | Rast |
| 2002/0123325 A1 | 9/2002 | Cooper |
| 2002/0144010 A1 | 10/2002 | Younis |
| 2002/0144079 A1 | 10/2002 | Willis et al. |
| 2003/0060188 A1 | 3/2003 | Gidron |
| 2003/0078754 A1 | 4/2003 | Hamza |
| 2003/0158614 A1 | 8/2003 | Friel |
| 2003/0204382 A1 | 10/2003 | Julier et al. |
| 2003/0212996 A1 | 11/2003 | Wolzien |
| 2004/0162064 A1 | 8/2004 | Himmelstein |
| 2004/0164228 A1 | 8/2004 | Fogg |
| 2005/0009506 A1 | 1/2005 | Smolentzov |
| 2005/0070221 A1 | 3/2005 | Upton |
| 2005/0130656 A1 | 6/2005 | Chen |
| 2005/0153654 A1 | 7/2005 | Anderson |
| 2005/0232469 A1 | 10/2005 | Schofield et al. |
| 2005/0251328 A1 | 11/2005 | Merwe et al. |
| 2005/0260984 A1 | 11/2005 | Karabinis |
| 2005/0275505 A1 | 12/2005 | Himmelstein |
| 2005/0278712 A1 | 12/2005 | Buskens et al. |
| 2006/0132357 A1 | 6/2006 | Pozgay et al. |
| 2006/0206576 A1 | 9/2006 | Obradovich et al. |
| 2006/0293829 A1 | 12/2006 | Cornwell et al. |
| 2007/0106133 A1 | 5/2007 | Satchwell et al. |
| 2007/0115868 A1 | 5/2007 | Chen |
| 2007/0115897 A1 | 5/2007 | Chen |
| 2007/0260372 A1 | 11/2007 | Langer |
| 2007/0260373 A1 | 11/2007 | Langer et al. |
| 2008/0021730 A1* | 1/2008 | Holla .................. G06F 19/3418 705/2 |
| 2008/0092140 A1 | 4/2008 | Doninger et al. |
| 2008/0154099 A1* | 6/2008 | Aspel .................. G06F 19/3418 600/301 |
| 2008/0169998 A1 | 7/2008 | Jacobsen et al. |
| 2009/0118590 A1 | 3/2009 | Teller et al. |
| 2009/0090592 A1 | 4/2009 | Mordukhovich |
| 2009/0240481 A1 | 9/2009 | Durrant-Whyte et al. |
| 2009/0268923 A1 | 10/2009 | Li |
| 2009/0268947 A1 | 10/2009 | Schaufler |
| 2009/0284378 A1 | 11/2009 | Ferren et al. |
| 2009/0319063 A1 | 12/2009 | Pan |
| 2010/0017543 A1 | 1/2010 | Preston et al. |
| 2010/0292556 A1* | 11/2010 | Golden ................ A61B 5/7465 600/364 |
| 2011/0167133 A1 | 7/2011 | Jain et al. |
| 2011/0212700 A1 | 9/2011 | Petite |
| 2011/0224501 A1 | 9/2011 | Hudsmith |
| 2012/0083971 A1 | 4/2012 | Preston et al. |
| 2012/0183153 A1 | 7/2012 | Preston et al. |
| 2014/0039804 A1 | 2/2014 | Park et al. |

(56) References Cited

U.S. PATENT DOCUMENTS

2014/0297311 A1* 10/2014 Jackson .............. G06F 19/3418
                                                                  705/2

FOREIGN PATENT DOCUMENTS

| DE | 19647283 A1 | 5/1997 |
| DE | 19922608 A1 | 11/2000 |
| DE | 19931161 | 1/2001 |
| EP | 0355490 B1 | 2/1990 |
| EP | 0 441 576 A2 | 8/1991 |
| EP | 0473866 A2 | 3/1992 |
| EP | 0 841 648 | 5/1998 |
| EP | 0841648 B1 | 5/1998 |
| EP | 1 355 128 | 8/2006 |
| GB | 2097563 | 11/1982 |
| JP | 10-076115 | 10/1999 |
| JP | 2000207691 | 7/2000 |
| KR | 1995-0017619 | 3/1999 |
| KR | 1999-021740 | 3/1999 |
| WO | WO9624229 | 8/1996 |
| WO | WO9908436 | 2/1999 |
| WO | WO9957662 | 11/1999 |
| WO | WO9965183 | 12/1999 |
| WO | WO 0029948 | 5/2000 |
| WO | WO 0079390 | 6/2000 |
| WO | WO0040038 | 7/2000 |
| WO | WO0130061 | 4/2001 |
| WO | WO0158110 | 8/2001 |
| WO | 2002/078538 A2 | 10/2002 |
| WO | WO/03/033092 | 4/2003 |

OTHER PUBLICATIONS

Ada 95 Transition Support—Lessons Learned, Sections 3, 4, and 5, CACI, Inc. -Federal, Nov. 15, 1996, 14 pages.
AMIC. Architecture specification release 1, 2001; 35 pages.
Bluetooth Doc; Advance Audio Distribution Profile Specification; Adopted version 1.0; dated May 22, 2003; 75 pages.
Bluetooth Doc; Audio/Video Remote Control Profile; Version 1.0 Adopted; dated May 22, 2003; 52 pages.
Bluetooth Hands-free Profile 1.5 Nov. 25, 2005.
Bluetooth Specification version 1.1; Feb. 22, 2001; 452 pages.
Boeing News Release, "Boeing Demonstrates JSF Avionics Multi-Sensor Fusion", Seattle, WA, May 9, 2000, pp. 1-2.
Boeing Statement, "Chairman and CEO Phil Condit on the JSF Decision", Washington, D.C., Oct. 26, 2001, pp. 1-2.
Counterair: The Cutting Edge, Ch. 2 "The Evolutionary Trajectory the Fighter Pilot—Here to Stay?" AF2025 v3c8-2, Dec. 1996, pp. 1-7.
Counterair: The Cutting Edge, Ch. 4 "The Virtual Trajectory Air Superiority without an "Air" Force?" AF2025 v3c8-4, Dec. 1996, pp. 1-12.
Embedded Bluetooth Migrates to Lisbon and Seattle; 11 pages; Jan. 23, 2008.
Green Hills Software, Inc., "The AdaMULTI 2000 Integrated Development Environment," Copyright 2002, printed Jul. 9, 2002; 7 pages.
H. Chung, L. Ojeda, and J. Borenstein, "Sensor Fusion for Mobile Robot Dead-reckoning with a Precision-calibrated Fiber Optic Gyroscope", 2001 IEEE International Conference on Robotics and Automation, Seoul, Korea, May 21-26, 2001, pp. 1-6.
Hitachi Automated Highway System (AHS), Automotive Products, Hitachi, Ltd., Copyright 1994-2002, 8 pages.
IEEE Standard for Information Technology—POSIX Based Supercomputing Application Environment Profile; Jun. 14, 1995, 72 pages.
ISIS Project: Sensor Fusion, Linkoping University Division of Automatic Control and Communication Systems in cooperation with SAAB (Dynamics and Aircraft), 2001, 18 pages.

J. Takezaki, N. Ueki, T. Minowa, H. Kondoh, "Support System for Safe Driving—A Step Toward ITS Autonomous Driving—", Hitachi Review, vol. 49, Nov. 3, 2000, pp. 1-8.
Joint Strike Fighter Terrain Database, ets-news.com "Simulator Solutions" 2002, 3 pages.
Luttge, Karsten; "E-Charging API: Outsource Charging to a Payment Service Provider"; IEEE; 2001 (pp. 216-222).
M. Chantler, G. Russel, and R. Dunbar, "Probabilistic Sensor Fusion for Reliable Workspace Sensing", Fourth IARP workshop on Underwater Robotics, Genoa, Nov. 1992, pp. 1-14.
MSRC Redacted Proposal, 3.0 Architecture Development, Aug. 29, 2002; pp. 1-43.
MyGig User Guide.
Powerpoint Presentation by Robert Allen—Boeing Phantom Works entitled "Real-Time Embedded Avionics System Security and COTS Operating Systems", Open Group Real-Time Forum, Jul. 18, 2001, 16 pages.
Product description of Raytheon Electronic Systems (ES), Copyright 2002, pp. 1-2.
Product description of Raytheon RT Secure, "Development Environment", Copyright 2001, pp. 1-2.
Product description of Raytheon RT Secure, "Embedded Hard Real-Time Secure Operating System", Copyright 2000, pp. 1-2.
S.G. Goodridge, "Multimedia Sensor Fusion for Intelligent Camera Control and Human-Computer Interaction", Dissertation submitted to the Graduate Faculty of North Carolina State University in partial fulfillment of the requirements for the degree of Doctor of Philosophy in Electrical Engineering, Raleigh, NC, 1997, pp. 1-5.
Specification of the Bluetooth System v1.0.B; Dec. 1, 1999.
Specification of the Bluetooth System v1.1; Feb. 22, 2001.
TNO FEL Annual Review 1998: Quality works, Observation Systems Division; "The Whole is More Than the Sum of its Parts"; 16 pages.
Vehicle Dynamics Lab, University of California, Berkeley, funded by BMW, current members: D. Caveney and B. Feldman, "Adaptive Cruise Control", at least as early as 2002, printed Jul. 2, 2002; 17 pages.
Stirling A: "Mobile Multimedia platforms" Vehicular Technology Conference Fall 2000. IEEE VTS Fall VTC2000. 52nd Vehicular Technology Conference (CAT. No. 00CH37152).
Nusser R. et al.: "Bluetooth-based wireless connectivity in an automotive environment" Vehicular Technology Conference Fall 2000. IEEE VTS Fall VTC2000 52nd Vehicular Techonlogy Conference (Cat. No. 00CH37152).
Martins e f v et al. "design of an OS9 operating system extension for a message-passing multiprocesor" Microprocessors and Microsystems, IPC Business Press LT. London, BG, vol. 21, No. 9, Apr. 1, 1998, pp. 533-543.
Gutierrez Garcia JJ et al. "Minimizing the effects of jitter in distributed hard real-time systems" Journal of Systems Architecture, Elsevier Science Publishers BV., Amsterdam, NL, vol. 41, No. 6/7. Dec. 15, 1996, pp. 431-447.
International Search Report for PCT/US02/020402; dated Apr. 3, 2003.
International Search Report for PCT/US02/020403; dated Jan. 27, 2003.
International Search Report for PCT/US02/016364; dated Feb. 14, 2003.
International Search Report for PCT/US02/016371; dated Aug. 18, 2003.
Robert Bosch GmbH, "CAN Specification, Version 2.0," Sep. 1991.
Wang, Z. et al. "A Message Priority Assignment Algorithm for CAN-based Networks," in CSC '92 Proceedings of the 1992 ACM Annual Conference on Communications, Mar. 1992.
Fay-Wolfe, et al., "Real-Time CORBA," IEEE Transactions on Parallel and Distributed Systems, vol. 11, Issue 10 (Oct. 2000).
Husein et al., "A Priority Based Service Algorithm for Use in Time-Critical and Integrated Services Networks," Proceedings of IEEE Singapore International Conference, vol. 1, pp. 93-97, 1993.
Release 1 Specification Set from the Automotive Multimedia Interface Collaboration (AMI-C), Jan. 2001.
Open Services Gateway Initiative (OSGi) Service Gateway Specification Release 1.0, May 2000.

(56) References Cited

OTHER PUBLICATIONS

Ellis, S. M., "Dynamic Software Reconfiguration for Fault-Tolerant Real-Time Avionic Systems," Microprocessor and Microsystems, Proceedings of the 1996 Avionics Conference and Exhibition, vol. 21, issue 1, pp. 29-39, Jul. 1997.

Peter Walzer, and Hans-Wilhelm Grove, "Integrated Research Volkswagen (IRVW) Futura," Passenger Car Meeting and Exposition, Dearborn, Michigan, Sep. 17-20, 1990.

Nace, W. & Koopman, P., "A Product Family Based Approach to Graceful Degradation," Proceedings of DIPES 2000, International IFIP WG 10.3/WG 10.4/ WG 10.5 Workshop on, Distributed and Parallel Embedded Systems, Paderborn University, Germany, Oct. 18-19, 2000.

Meredith Beveridge, "M.S. Project Report, Jini on the Control Area Network (CAN): A Case Study in Portability Failure", Department of Electrical and Computer Engineering, Carnegie Mellon University, Phil Koopman-advisor, Mar. 2001.

Universal Serial Bus Specification, Revision 1.1, Compaq, Intel, Microsoft and NEC, Sep. 23, 1998.

Universal Serial Bus Specification, Revision 2.0, Compaq, Hewlett-Packard, Intel, Lucent, Microsoft, NEC and Philips, Apr. 27, 2000.

Tindell, Ken, et al, "A CAN Communications Concept with Guaranteed Message Latencies", Oct. 1998.

Robinson, Ralph L., "An Open Versus Closed Architecture for Multimedia Systems," Proceedings of the 2000 International Congress on Transportation Electronics, pp. 445-450, Oct. 2000.

Y. Chubachi and H. Okagaki, "The Development of Traffic Information System Using AutoPC," Proceedings of the 2000 International Congress on Transportation Electronics, pp. 81-88, Oct. 2000.

USBlyzer, "Brief Overview of USB History".

M. Tchorowski and J. Mate, "Avionics and Automotive bandwagon flying together on the infotronics Highway," Proceedings of the 1998 International Congress on Transportation Electronics, pp. 351-354, Oct. 1998.

Fout, Tom, "Universal Plug and Play in Windows XP," Jul. 1, 2001.

Yen, H.W., et al., "Information Security and Integrity in Network Vehicle," Proceedings of the 1998 International Congress on Transportation Electronics, pp. 319-323, Oct. 1998.

Minagawa, Shoichi, et al, "Open Architectural Car Multimedia Platform," Proceedings of the 1998 International Congress on Transportation Electronics, pp. 198-194 Oct. 1998.

Kanemitsu, Dean et al. "Productivitys Next Dimension—The Mobile Office Computing Platform," Proceedings of the 2000 International Congress on Transportation Electronics, pp. 159-165, Oct. 2000.

Bhaskaran, Parvathy, "Reinventing the Car Radio for the Internet—the iRadio™," Proceedings of the 2000, International Congress on Transportation Electronics, pp. 147-153, Oct. 2000.

Buckley, Stephen, et al., "The Car as a Peripheral-Adapting a Portable Computer to a Vehicle Intranet," Proceedings of the 1998 International Congress on Transportation Electronics, pp. 211-217, Oct. 1998.

Arnold, Ken, et al., "The Jini Specification," Publisher Addison-Wesley, 1999.

Powers, Chuck, et al., Today's Electronics in Todays Vehicles, Proceedings of the 1998 International Congress on Transportation Electronics, pp. 195-200, Oct. 1998.

Vaught, Mark A., "Phone-Activated Auto-Muting Circuit," Jan. 1990.

Clarion Co. Ltd., "Clarion AutoPC 310C Owner's Manual," 1998.

Clarion, "2002 Clarion Product Catalog Car Audio, Multimedia, Marine, and Security Retail Products," 2002.

Clarion Co., Ltd., "Joyride Quick Reference Guide," 2000-2001.

Joyride, Windows CE System Software User's Manual, 1999-2001.

Lind, R., et al., "The Network Vehicle—A Glimpse into the Future of Mobile Multi-Media," IEEE AES Systems Magazine, Sep. 1999.

Arun Ayyagari, Bluetooth ESDP for UPnP, Published Jan. 31, 2001.

First Amended Complaint and Answer from *Eagle Harbor Holdings, LLC, and Mediustech, LLC*, v. *Ford Motor Company*, Washington Western District Court, Case No. 3:11-CV-05503-BHS, Case filed: Jun. 30, 2011.

Exhibits and Modules from *Eagle Harbor Holdings, LLC, and Mediustech, LLC*, v. *Ford Motor Company*, Washington Western District Court, Case No. 3:11-CV-05503-BHS, Case filed: Jun. 30, 2011.

Longbin, Xiaoquain, Yizu Kang, Bar-Shalom: Unbiased converted measurements for tracking; IEEE Transactions on Aerospace and Electronic Systems vol. 34(4), Jul. 1998, pp. 1023-1027.

Miller, Drummond: Comparison of methodologies for mitigating coordinate transformation basis in target tracking; Proceedings SPIE Conference on Signal and Data Processing of Small Targets 2000, vol. 4048, Jul. 2002, pp. 414-426.

Duan, Han, Rong Li: Comments on "Unbiased (debiased) converted measurements for tracking" IEEE Transactions on Aerospace and Electronic Systems, vol. 40(4), Oct. 2004, pp. 1374-1377.

USPTO, Office Action for U.S. Appl. No. 14/981,616 dated Sep. 30, 2016.

USPTO, Office Action for U.S. Appl. No. 14/981,616 dated May 17, 2017.

\* cited by examiner

METHOD AND APPARATUS FOR DYNAMIC CONFIGURATION OF A MULTIPROCESSOR HEALTH DATA SYSTEM

RELATED APPLICATION DATA

This application is a nonprovisional of provisional application Ser. No. 62/154,245 filed Apr. 29, 2015, titled—METHOD AND APPARATUS FOR DYNAMIC CONFIGURATION OF A MULTIPROCESSOR HEALTH DATA SYSTEM. This application is a continuation in part of patent application Ser. No. 14/981,616 filed Dec. 28, 2015, titled—METHOD AND SYSTEM FOR DYNAMIC CONFIGURATION OF MULTIPROCESSOR SYSTEM, which is a continuation of patent application Ser. No. 14/255,435 filed Apr. 17, 2014, now U.S. Pat. No. 9,292,334, issued Mar. 22, 2016, titled—METHOD AND APPARATUS FOR DYNAMIC CONFIGURATION OF MULTIPROCESSOR SYSTEM, which is a continuation of patent application Ser. No. 12/979,198 filed Dec. 27, 2010, now U.S. Pat. No. 8,744,672, issued Jun. 3, 2014, titled—METHOD AND APPARATUS FOR DYNAMIC CONFIGURATION OF MULTIPROCESSOR SYSTEM, which is a division of patent application Ser. No. 12/483,214 filed Jun. 11, 2009, now U.S. Pat. No. 8,958,315, issued Feb. 17, 2015, titled—METHOD AND APPARATUS FOR DYNAMIC CONFIGURATION OF MULTIPROCESSOR SYSTEM, which is a continuation of patent application Ser. No. 11/462,958, filed Aug. 7, 2006, now U.S. Pat. No. 7,778,739 issued Jul. 28, 2010 Titled—METHOD AND APPARATUS FOR DYNAMIC CONFIGURATION OF MULTIPROCESSOR SYSTEM, which is a continuation of patent application Ser. No. 09/841,915, filed Apr. 24, 2001, now U.S. Pat. No. 7,146,260 issued Dec. 5, 2006 titled—METHOD AND APPARATUS FOR DYNAMIC CONFIGURATION OF MULTIPROCESSOR SYSTEM, all of which are hereby incorporated by reference in their entirety. Additionally, the present application incorporates by reference U.S. Pat. No. 6,629,033, issued Sep. 30, 2003 titled—OPEN COMMUNICATION SYSTEM FOR REAL-TIME MULTIPROCESSOR APPLICATIONS, and U.S. Pat. No. 7,178,049, issued Feb. 13, 2007 titled—METHOD FOR MULTI-TASKING MULTIPLE JAVA VIRTUAL MACHINES IN A SECURE ENVIRONMENT; both U.S. Pat. No. 6,629,033 and U.S. Pat. No. 7,178,049 are hereby incorporated by reference in their entirety.

BACKGROUND OF THE INVENTION

This invention relates to a system and method for overall health and fitness monitoring, analysis, and reporting.

As background, from the U.S. Pat. No. 7,146,260 patent specification, which is incorporated by reference in the related application data section above, it should be understood that the multiprocessor system described in the U.S. Pat. No. 7,146,260 patent could be used in applications other than cars, as described in column 8, lines 38-48 of the '260. For example, FIG. 13 of the U.S. Pat. No. 7,146,260 shows a first GUI 212 that shows different processors and applications in appliances that are coupled together using the DC system 10 in a home network. Examples include appliance systems, electronic security systems, radios, Compact Disc (CD) players, internal and external lighting systems, temperature control systems, locking systems, etc. In another example, the dynamic configuration system could be used in the healthcare industry, particularly in wireless health data monitoring systems for aggregating certain health data for a user.

Improving and maintaining a user's health involves diligent and tedious monitoring of many critical health and fitness related components. For the average user, reduced time and motivation hampers the ability to track and manage personal health and fitness data. Currently there are numerous websites and applications that monitor only a portion of the health and fitness data, making it difficult for the user to examine their overall health. Consolidating all forms of health data into a manageable format will have benefits for those seeking better fitness and better medical care and insurance by creating a more complete picture of a user's health and wellness. In addition to the user's benefits, accessible health information will improve medical care. Allowing health care professionals the ability to observe lifestyles will lead to improved diagnosis of ailments, recommendations on healthy lifestyle changes, and improved emergency response.

DESCRIPTION OF RELATED ART

In a discussion of prior art, U.S. patent application Ser. No. 11/925,902 filed Oct. 27, 2007, titled MULTI-SENSOR SYSTEM, DEVICE, AND METHOD FOR DERIVING HUMAN STATUS INFORMATION generally describes a wireless communications device, such as a cellular telephone, having sensors to generate data indicative of a physiological or contextual parameters of a user. A processor on the wireless communications device is adapted derive physiological state information of the user from the contextual or physiological parameters. The apparatus may include a central monitoring unit remote from the sensors for storing data and transmitting data to a recipient. What this application did not disclose is the ability to provide feedback to a local application or device based on desired information, the ability to communicate with other devices and/or running applications, the ability to selectively connect to other devices or applications via user input or set preferences, the ability to request data from outside sources, and the ability to upload health and fitness related data to websites and/or social platforms.

In a discussion of prior art, U.S. patent application Ser. No. 13/046,707 filed Mar. 12, 2011, titled IN-HOME HEALTH MONITORING APPARATUS AND SYSTEM generally describes a health monitoring system that allows users to maintain an autonomous lifestyle while providing health observation and reporting for family members, caregivers, and healthcare professionals. The system is supported by a network for critical, round-the-clock health monitoring and remote care, and may be used in the home or elsewhere. In one exemplary embodiment, the system comprises a touch-screen computing device that also may function as a television and video or DVD player, and provides a series of service options for users. The computing device is connected to a network and/or the Internet. What this application did not disclose is the ability to monitor, record, and recommend health and fitness information, the ability to connect to multiple devices such as televisions and personal computers, and the ability to collect, analyze and provide feedback to the user based on surrounding environmental data.

In a discussion of prior art, U.S. patent publication Ser. No. 10/445,275 filed May 23, 2003, titled REAL-TIME MEDICAL MONITORING APPLICATION WITH A NETWORK INTERFACE DEVICE generally describes systems and methods provided for medical monitoring of a patient at a patient premises. A medical-data collection device is adapted to collect medical data from the patient. The medical-data collection device is interfaced with a transport medium internal to the patient premises. A network interface device is also provided with multiple application devices interfaced with the transport medium internal to the patient premises. One of the application devices is a medical-monitoring application device adapted to process the collected medical data. Another of the application devices is adapted to exchange data with a transport medium external to the patient premises. A processor in communication with the application devices is adapted to coordinate transmission of the collected medical data over the transport medium external to the patient premises. What this application did not disclose is the ability to communicate with other devices such as televisions or personal computers, the ability to upload health and fitness related data to websites and/or social platforms, the ability to collect data outside the user's primary premises, and the ability to collect data related to health and fitness.

In a discussion of prior art, U.S. patent application Ser. No. 09/602,537 filed Jun. 23, 2000, titled SYSTEM FOR MONITORING HEALTH, WELLNESS AND FITNESS generally describes a system for detecting, monitoring and reporting physiological information includes a sensor device adapted to be worn on the upper arm that includes at least one of an accelerometer, a GSR sensor and a heat flux sensor and generates data indicative of at least one of activity, galvanic skin response and heat flow. The sensor device may also generate derived data from at least a portion of the data indicative of at least one of activity, galvanic skin response and heat flow. The system includes a central monitoring unit that generates analytical status data from at least one of the data indicative of at least one of activity, galvanic skin response and heat flow, the derived data, and previously generated analytical status data, a means for establishing electronic communication between the sensor device and the central monitoring unit, and a means for transmitting data to a recipient. What this application did not disclose is the ability to collect data from remote devices that are not worn on the body, the ability to recall information running on a second device or service application, the ability to diagnose users based on collected data, and the ability to set preferences to differentiate and consolidate data.

In a discussion of prior art, non-patent literature WEBMD that describes a corporation which provides health information as a service. WEBMD has information regarding health and health care, including a symptom checklist, pharmacy information, "drugs information", blogs of physicians with specific topics, and a place to store personal medical information. The functions that WEBMD does not perform include tracking and automatic collection of data from users, providing feedback to applications or devices, connecting users to health professionals or peer networks, and generating feedback outside of a visual display.

What is needed is an application to monitor, aggregate, and relay health, fitness, nutrition, and environmental data from data generated by both contact and noncontact sensors, an application with the ability to communicate with other devices running a service application, the ability to connect to social platforms, the ability to connect and access data and feedback on multiple devices and applications, the ability to set preferences based on user goals, and the ability to restrict third party access to collected data.

With respect now to the aggregation and collection of data from wireless devices, and in a further discussion of prior art U.S. patent application Ser. No. 10/578,710 filed Nov. 18, 2004, titled MONITORING OF VITAL SIGNS AND PERFORMANCE LEVELS which generally describes a monitoring device for monitoring vital signs which includes a housing. Signal input components are positioned in the housing to receive an electrical signal carrying data representing at least one vital sign of a subject. Wireless communications circuitry is mounted in the housing and is connected to the input components for transmitting and receiving wireless signals. Additionally, U.S. patent application Ser. No. 12/652,377 filed Jan. 5, 2010 titled SYSTEM, METHOD, AND DEVICE FOR MEDICAL DEVICE DATA CAPTURE AND PROCESSING, which generally discloses a system, method, and computer-readable medium for medical device data capture and processing having an application hosting device configured to modify data received from a medical device. A data processing server receives the modified data from the application hosting device and associates the modified data with a user, the medical device and/or the application hosting device. Another aspect provides an application hosting device that receives instructions relating to the medical device and transmits the instructions to the medical device. A data processing server receives the instructions relating to the medical device from a user and to transmit the instructions to the application hosting device. The data processing server receives the data from the application hosting device. Another aspect provides an application hosting device that includes a processor and a memory. Data relating to a plurality of users and a plurality of medical devices is stored in the memory.

Both of these applications and specifications fail to disclose a secure simple method of pairing a Bluetooth device to the data collection system. It was not known in the art of Bluetooth until 2007 when the Bluetooth Core Specification Version 2.1+EDR was published and adopted by the Bluetooth SIG on 26 Jul. 2007. The headline feature of 2.1 is Secure Simple Pairing (SSP) which was implemented to improve the pairing experience for Bluetooth devices while increasing the use and strength of security. Version 2.1 also allows various other improvements, including "Extended inquiry response" (EIR), which provides more information during the inquiry procedure to allow better filtering of devices before connection. U.S. Pat. No. 7,146,260 and its family of patents, claiming priority to Apr. 24, 2001, discloses and claims the steps of SSP as summarized below.

This application is filed as a continuation in part disclosing a METHOD AND APPARATUS FOR DYNAMIC CONFIGURATION OF A MULTIPROCESSOR HEALTH DATA SYSTEM; one reliant on the Secure Simple Pairing of portable health data devices and processors. So as to reduce the complexity and length of the Detailed Specification, and to fully establish the state of the art in certain areas of technology, Applicant(s) herein expressly incorporate(s) by reference all of the following materials identified in each numbered paragraph below.

To those skilled in the art of wireless network systems, and particularly Bluetooth wireless systems, will recognize the '260 disclosure of April 2001 and the DCS described became known in the art of Bluetooth as "Secure Simple Pairing" in the Jul. 26, 2007 release of the Bluetooth Specification 2.1+EDR. In the discussion of architecture in Part A—Architecture page 131 of 1420, " . . . The primary goal of Secure Simple Pairing is to simplify the pairing procedure for the user. Secondary goals are to maintain or improve the security in Bluetooth wireless technology. Since high levels of security and ease-of-use are often at opposite ends of the spectrum in many technologies and products, much care has been taken to maximize security while minimizing complexity from the end user's point of view." This was the first time a dynamic configuration system was specified by Bluetooth, therefore: specification of the Bluetooth System Versions: 1.2 dated Nov. 5, 2003; 2.0+EDR dated Nov. 4, 2004; 2.1+EDR dated Jul. 26, 2007; 3.0+HS dated Apr. 21, 2009; and 4.0, dated 17 Dec. 2009 is incorporated by reference and is therefore not described in further detail. IEEE 802.11n specification for Wireless Local Area Networks dated 29 Sep. 2009 is incorporated by reference and is therefore not described in further detail.

Additionally, the U.S. Pat. No. 7,146,260 ('260) specification which has been incorporated by reference describing a dynamic configuration system for wired and wireless devices, among other disclosures. Specifically '260 generally discloses the steps of secure simple pairing for Bluetooth through the implementation of some or all of the steps of the Dynamic Configuration system; where the dynamic configuration system has multiple processors configured to operate together, including one or more of the processors coupled together into a multiprocessor network. At least one processor in the multiprocessor network is configured to operate a Bluetooth transceiver which is configured to detect and establish communication between the multiprocessor network and the new device in proximity to the multiprocessor network. Once detected, selectively connect the new device to the multiprocessor network, use a data manager to identify a particular type of data used in the new device and processed with a first software application controlled and operated by the new device. Once a particular type of data is identified, identify a second software application from among multiple different software applications located in a memory in the multiprocessor network, where the second software application is currently not loaded in or operated by any of the on-board processors, and the second software application is also configured to process the same particular type of data processed by the first software application controlled and operated by the new device. Using the data manager, select or use a pre-selected processor in the multiprocessor network for operating the second software application. Once selected, automatically move the second software application from the memory in the multiprocessor network to the processors selected. Configure the selected processors to run the second software application, where running the second software application causes the selected processors to take over control and operation of the new device including initiating transfer of the data from the new device. The foregoing steps of securely adding a new device to a system of one or more processors is called a Dynamic Configuration System or DCS. Once a health device is securely connected, operate a logging manager in at least one of the multiprocessors configured to monitor data from the processors and identify certain data for logging from the processors, wherein the certain data is logged from different health sensors. Once logged, the health data is stored in a data memory, wherein the stored data is based on a pre-determined condition and responds to an outgoing message from one of the health applications for sending out over the Bluetooth link to another processor, wherein the logging manager sends at least a portion of the logged certain data retrieved from the data memory based on the pre-determined condition.

Applicants believe that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), applicants will amend the specification to expressly recite the essential material that is incorporated by reference as allowed by the applicable rules.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and/ordinary meaning of terms in the specification and claims unless they clearly state otherwise and then further, expressly set forth the "special" definition of that term and explain how it differs from the plain and/ordinary meaning. Absent such clear statements of intent to apply a "special" definition, it is the inventors' intent and desire that the simple, plain and/ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and/ordinary English meaning to those skilled in the applicable arts as set forth above.

Further, the inventors are fully informed of the standards and application of the special provisions of 35 U.S.C. § 112, ¶6. Thus, the use of the words "function," "means" or "step" in the Detailed Description or Description of the Drawings or claims is not intended to somehow indicate a desire to invoke the special provisions of 35 U.S.C. § 112, ¶6, to define the invention. To the contrary, if the provisions of 35 U.S.C. § 112, ¶6 are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112, ¶6. Moreover, even if the provisions of 35 U.S.C. § 112, ¶6 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

BRIEF DESCRIPTION OF THE DRAWINGS

A more complete understanding of the present invention may be derived by referring to the detailed description when considered in connection with the following illustrative figures. In the figures, like reference numbers refer to like elements or acts throughout the figures.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

The data collected by the application comes from multiple data generating devices that are present in everyday living environments comprising at least one of a home, car, gym, and workplace. The local application can be run on one of a smartphone, personal PC, tablet, or standalone unit. The application collects static or dynamic data that can be stored, processed or recalled as information. As the user goes about normal routines of the day, the application collects selected data relevant to the user. The application identifies data generated by a device and/organizes the data into user selected categories. The user has control over what information can be accessed by third parties and how the information is relayed. Users can also select format and interaction methods of feedback. The local application can be used to recall information from any combination of services about health, fitness, nutrition, or medicine. The application can track the user's nutrition, workout performance, medicine consumption, environmental conditions, and personal changes. The application can continuously monitor a user in an environment and provide feedback on the user's status in the environment.

Figure 1:
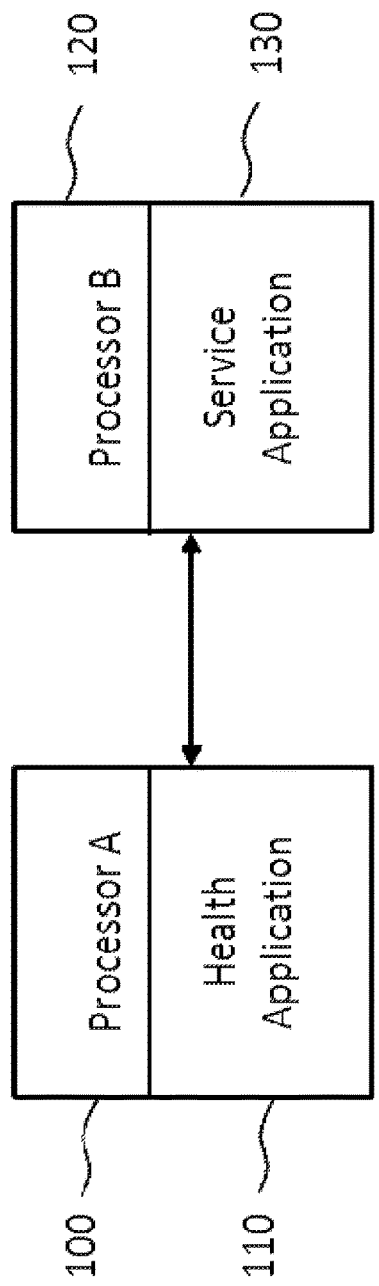
FIG. 1 is a diagram of the connection between the health application running on processor A and a service application running on processor B.

FIG. 1 depicts a connection between the health application 110, running on processor A 100, and the service application 130, running on processor B 120. The health application 110 communicates with the service application 130 to transmit collected data from the data generating devices and to obtain requested data. The health application 110 is capable of processing or storing data itself or sending data to the service application 130 for processing or storage.

Figure 2:
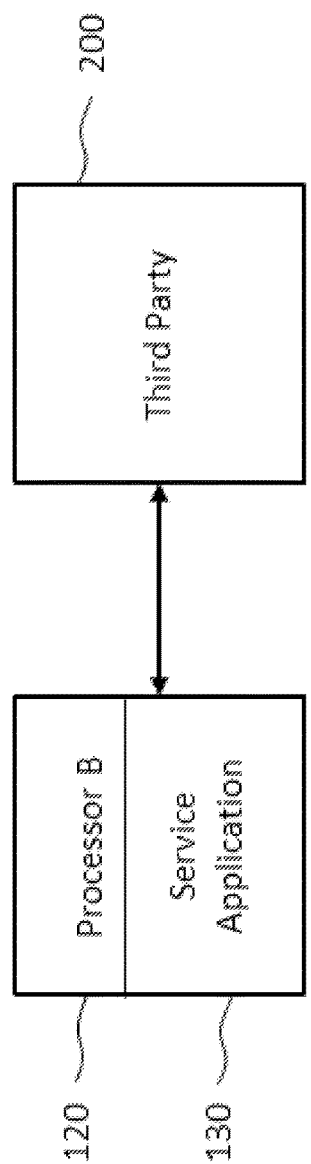
FIG. 2 is a diagram of the service application connecting to a third party.

FIG. 2 depicts the service application 130, running on processor B 120, communicating with a third party 200. The third party 200 may be one of a social platform, a health professional, a database, and a site providing health, fitness, and/or nutritional information. The service application 130 can either process the information or transmit the data to a third party 200 for processing and/or feedback. The third party 200 relays the processed data and/or feedback to the service application 130.

Figure 3:
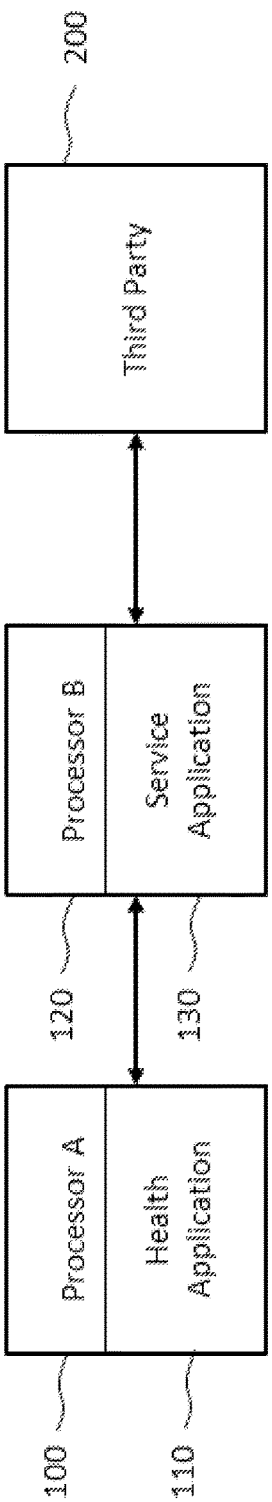
FIG. 3 is a diagram of the communication between the health application, running on processor A, the service application, running on processor B, and a third party.

FIG. 3 depicts the communication between the health application 110 running on processor A 100, the service application 130 running on processor B 120, and a third party 200. Both the health application 110 and the service application 130 can be interacted with by one of a user, an authorized doctor, personal trainer, nutritionist, family member, or any other entity the user selects. The user is able to specify who may interact with their data and which data the other entities are allowed to review. For instance, the user may restrict a nutritionist to only be able to review data relating to the user's nutrition. The user may also restrict the time frame in which another entity may review their data. For instance, the user may choose to permit access to his overall health data by a doctor only for the duration of an appointment.

Figure 4:
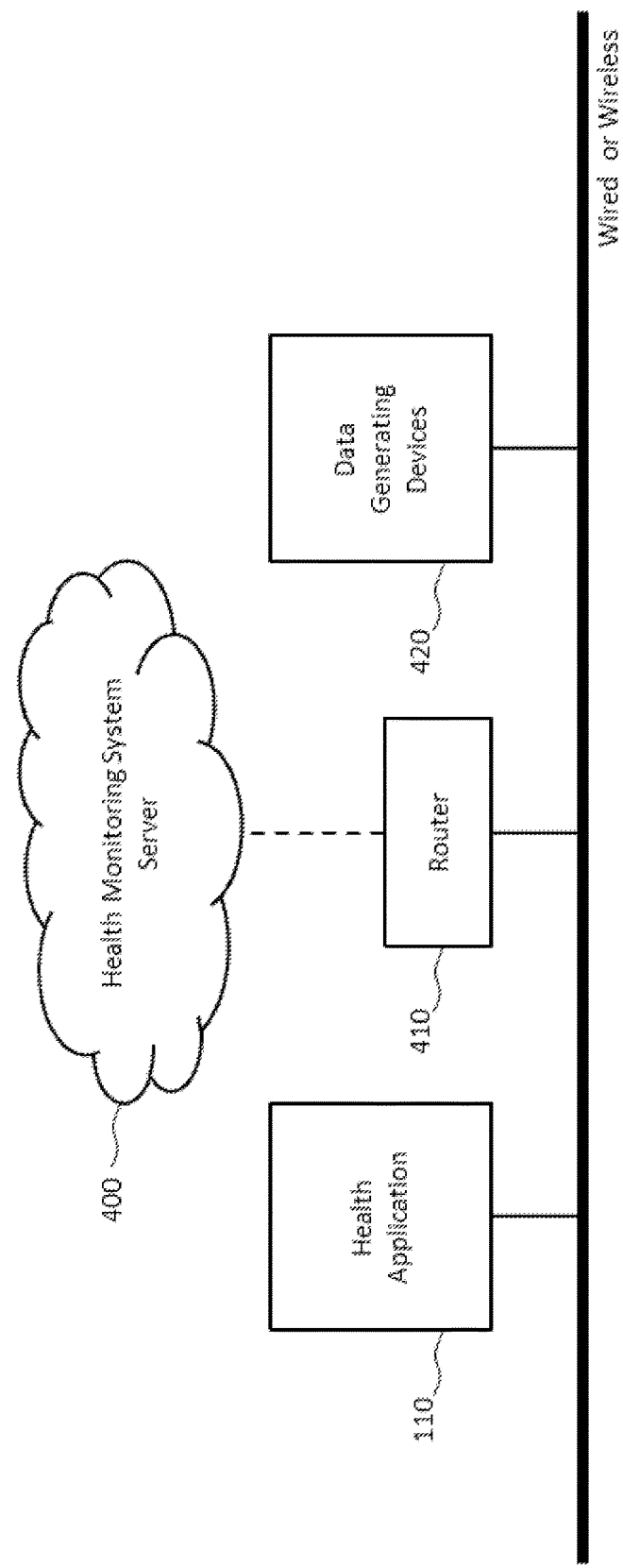
FIG. 4 is a diagram depicting how a health application can be connected to various data generating devices and a method to transmit data to a server.

FIG. 4 depicts the health application 110 collecting data from data generating devices 420. The health application 110 runs on one of a smartphone, tablet, personal computer, or standalone device designed with a processor to run the health application 110. The health application 110 can run on any device capable of joining or creating networks so as to transmit and receive data. The devices connected to the health application 110 have the capability of sending, receiving, storing, and transmitting data packets through a router 410 to a health monitoring system server 400 located locally or in the cloud. The health monitoring system server 400 can send one of data or requested information to the health application 110. Devices may be connected by one of wired or wireless networks. The communication between the health application 110 and a data generating device 420 consists of sending and receiving data packets comprising one of static and dynamic data, and device 420 updates.

Figure 5:
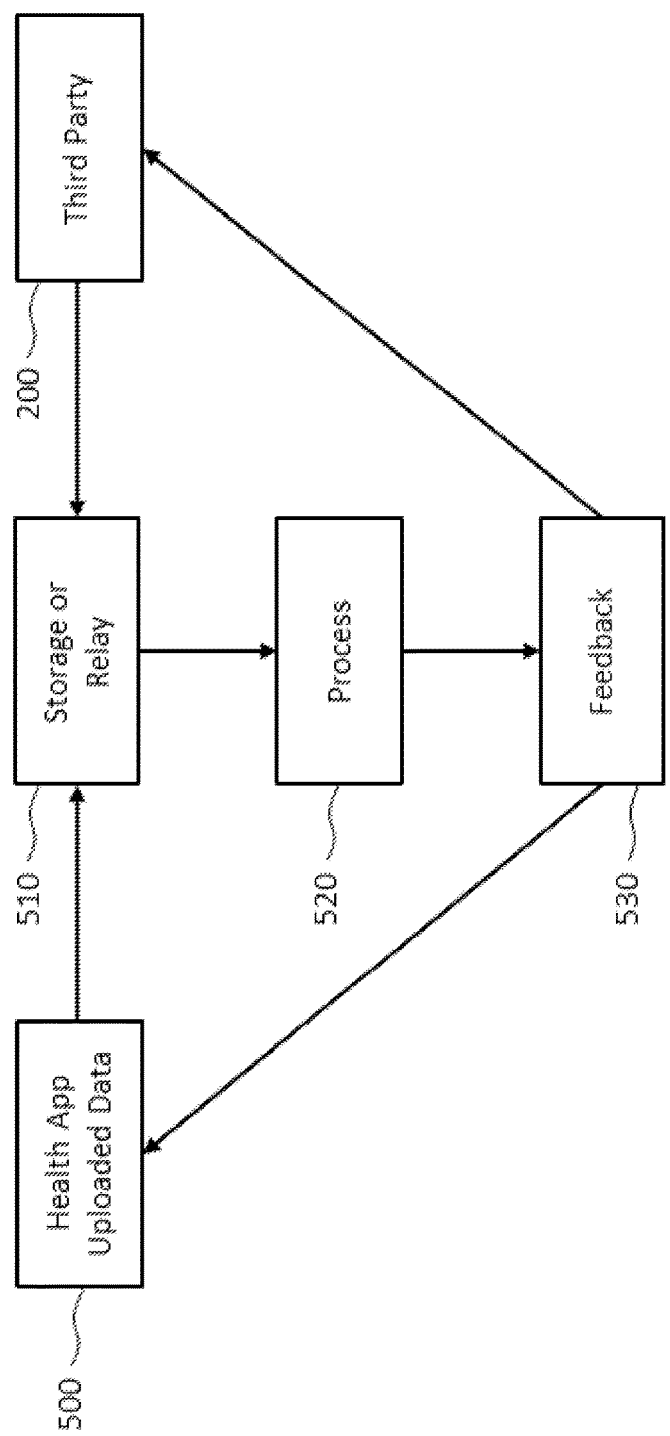
FIG. 5 is a diagram of the service application receiving, transmitting and processing data.

FIG. 5 depicts the service application 130 (FIG. 1) obtaining data from the health application 110 (FIG. 1) and/or a third party 200, processing 520, and transmitting the data. Data obtained by the health application 110 (FIG. 1) is uploaded 500 to the service application 130 (FIG. 1). Based on user preferences the service application 130 (FIG. 1) can perform one of store 510, process 520 or transmit the data to a third party 200. If a third party 200 is processing the data, the processed data will transfer back to the service application 130 (FIG. 1) and the service application 130 (FIG. 1) will either store 510 the data or transmit the data back to the health application 110 (FIG. 1). When the data has been processed 520 by one of a third party 200 or the service application 130 (FIG. 1), the service application 130 (FIG. 1) will relay feedback 530 back to one of third party 200 and/or the health application 110 (FIG. 1).

Figure 6:
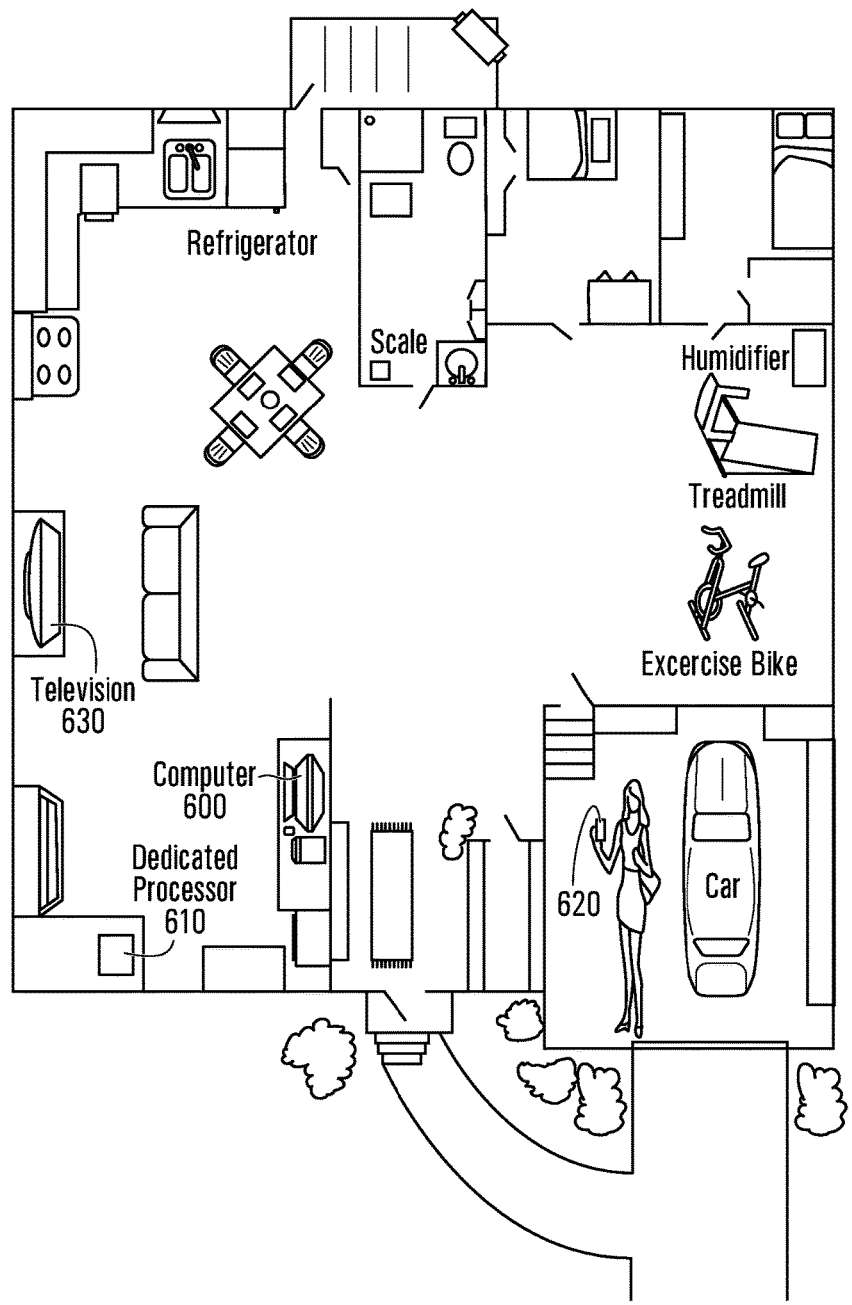
FIG. 6 illustrates the health application and service application collecting data from multiple data generating devices located in a typical home.

FIG. 6 depicts devices running the health application 110 (FIG. 1) or service application 130 (FIG. 1). The devices may comprise a smartphone 620, a computer 600, a television 630, scale, refrigerator, humidifier, treadmill, exercise bike, and vehicle. Based on user preferences, each device has the capability of running the health application 110 (FIG. 1) and the service application 130 (FIG. 1) concurrently or individually. A personal smartphone 620 can run the service application 130 (FIG. 1) when a dedicated processor 610 or a computer 600 running the health application 110 (FIG. 1) is present. The smartphone 620 is capable of running the health application 110 (FIG. 1) when the dedicated processor 100 running the health application 110 (FIG. 1) is out of range. The health data collected by the smartphone 620 when running the health application 110 (FIG. 1) can be transferred to a dedicated processor 100 running the health application 110 (FIG. 1) when it comes within range.

Figure 7:
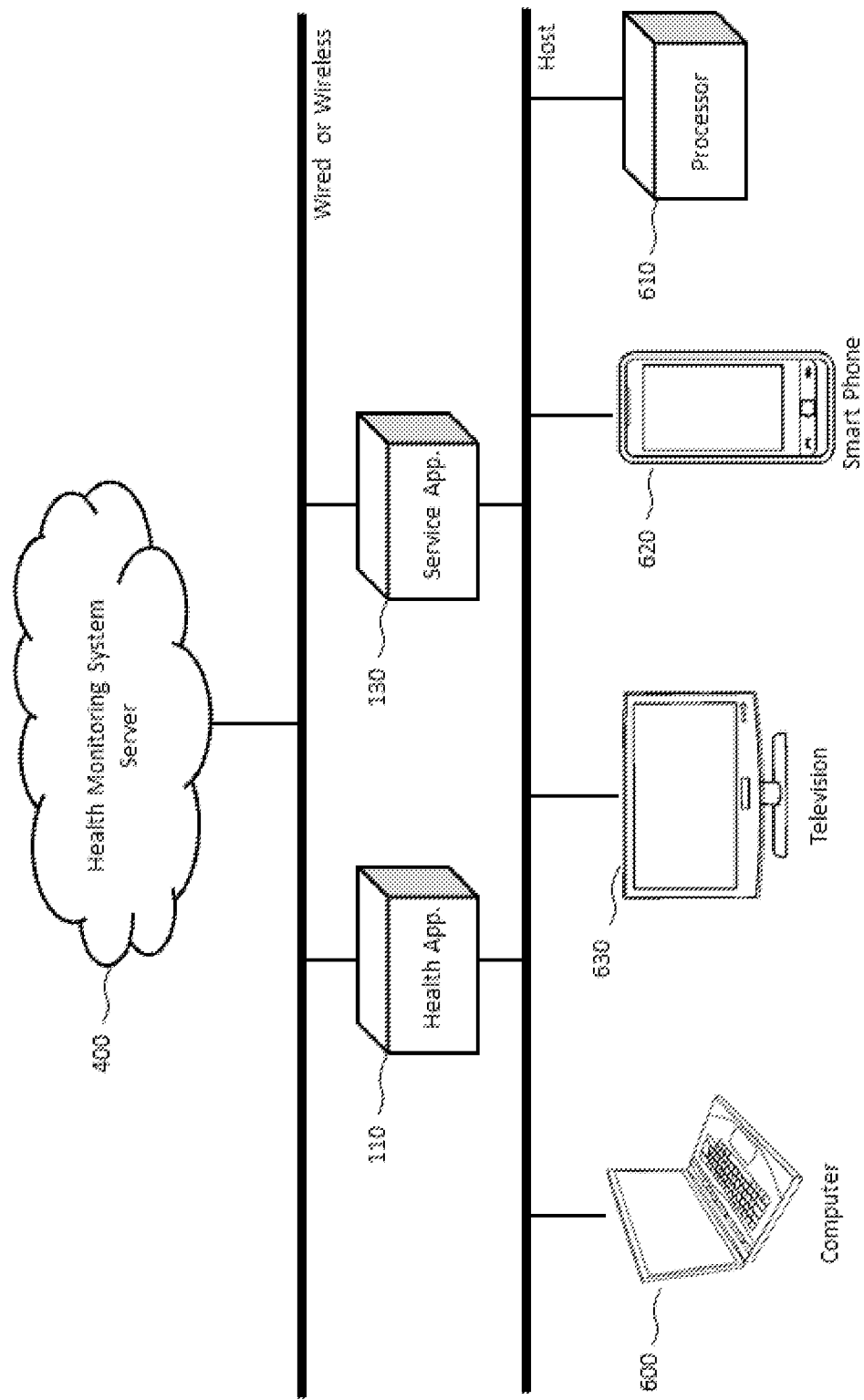
FIG. 7 is a diagram depicting communication between applications, devices, and the server.

FIG. 7 depicts how the health application 110 and service application 130 can operate on multiple devices and selectively connect and communicate with each other and the health monitoring system server 400. The device running one of the health application 110 and the service application 130 is one of a standalone device with a processor 610, the cloud 400, a computer 600, a television 630, and a smartphone 620. The device collecting the data runs the health application 110 and is capable of receiving, transmitting, or processing the health data and information. The data generating devices 420 (FIG. 4) can connect to any device running the health application 110, which may then transmit data to a service application 130, running either locally or on the health monitoring system server 400. The health monitoring service can be located on one of health monitoring system server 400 or a network based service. The communication can be relayed by one of wired or wireless methods between the data stored on the server and the health application 110. The health monitoring system server 400 and the health application 110 are capable of communicating with external sources including one of social media, SMS messages, email, and other notification techniques.

Figure 8:
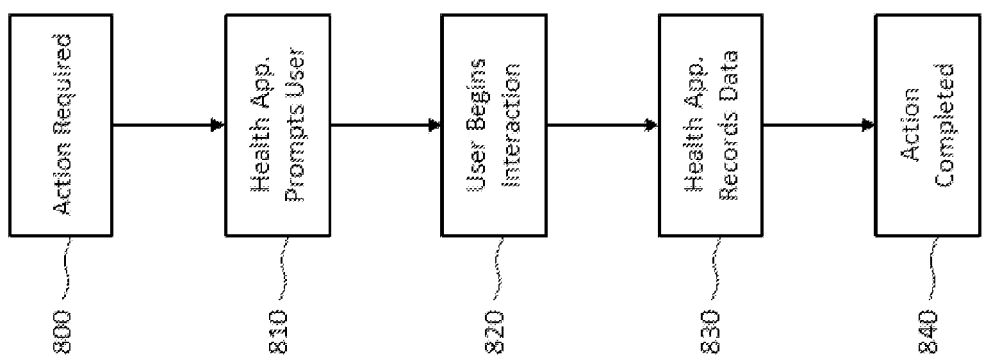
FIG. 8 is a diagram depicting a process for collecting health data after the user has been prompted for input by the health application.

FIG. 8 depicts a user being prompted by the health application 110 (FIG. 1) to perform or acknowledge a required action 800. Based on user preferences, the health application 110 (FIG. 1) can prompt the user 810 by a notification. The user can interact 820 with the notification by one of performing, dismissing, or resetting the required action. The health application 110 (FIG. 1) can recognize the action taken by one of the activation of a data generating device 420 (FIG. 4) and/or user response. When a data generating device 420 (FIG. 4) is in use, the health application 110 (FIG. 1) can record 830 the data and provide feedback to the user.

Figure 9:
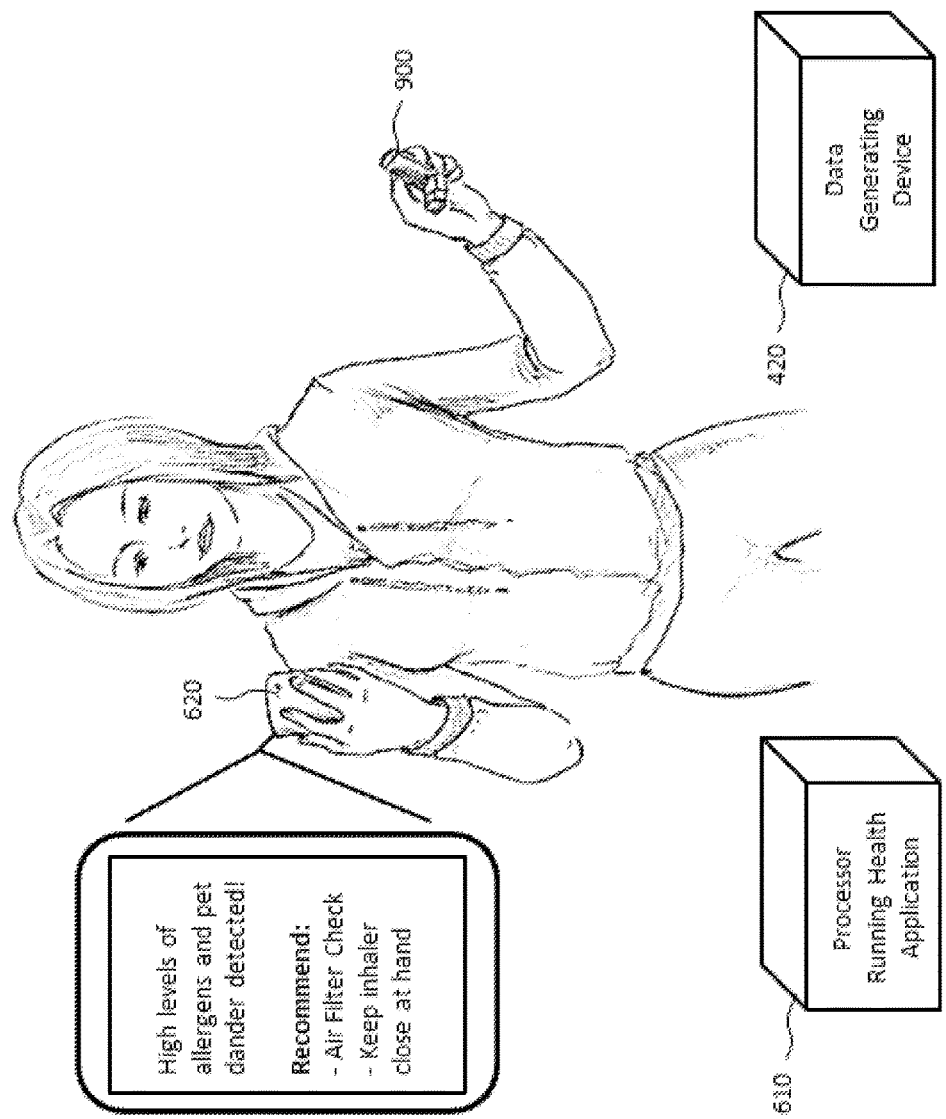
FIG. 9 illustrates a user being notified by the service application running on a smartphone to locate and possibly use an inhaler based on collected environmental data.

FIG. 9 illustrates a user being notified by one of a health application 110 (FIG. 1) and service application 130 (FIG. 1) running on the smartphone 620 to advise the use of an inhaler 900 based on the analyzed environmental data obtained from a data generating device 420. The dedicated processer 610 running the health application continuously collects and analyzes environmental data. The dedicated processor 610 running the health application transmits a notification to the smartphone 620 running one of a health application 110 (FIG. 1) or service application 130 (FIG. 1) advising the use of an inhaler 900. The environmental data can be analyzed by one of health application 110 (FIG. 1), service application 130 (FIG. 1) and third party 200 (FIG. 2) and generate feedback based on the analysis.

Figure 10:
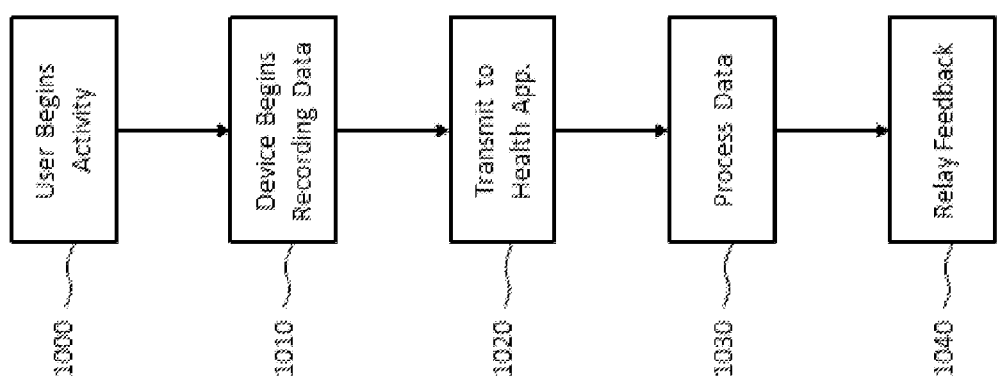
FIG. 10 is a diagram depicting a user prompting the health application to begin collecting health data from a data generating device.

FIG. 10 depicts initialization 1000 of the health application 110 (FIG. 1) by a user to collect and analyze health data obtained from a data generating device 420 (FIG. 4). The activation of the health data generating device 1000 by the user prompts the health application 110 (FIG. 1) to begin recording or process data 1010. Based on user preferences, the recording session 1010 can be initiated by interacting with the health application 110 (FIG. 1) or the data generating device 420 (FIG. 4). When a data generating device 420 (FIG. 4) is in use the data is recorded 1010, transmitted to the health application 1020, processed by the health application 1030, and feedback is relayed to the user 1040.

Figure 11:
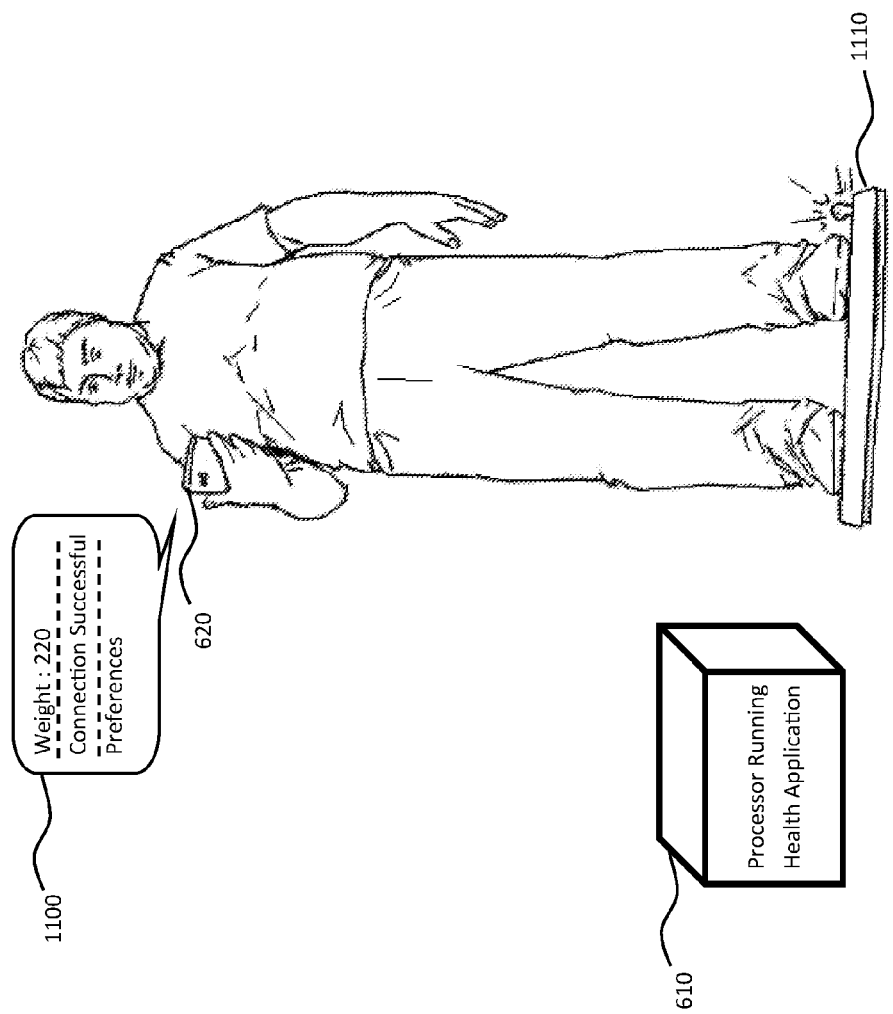
FIG. 11 illustrates the health application being prompted by the user through the activation of a data generating device and relaying user information to a smartphone.

FIG. 11 depicts a user measuring his body parameters with a wireless scale 1110 and transmitting the data to a dedicated processor 610 running the health application. The data is then relayed to the smartphone 620, running the service application 130 (FIG. 1). The health application 110 (FIG. 1) is capable of identifying the user that is on the wireless scale 1110 when the measurements are recorded. A secure connection is established between the wireless scale 1110 and the dedicated processor 610 running the health application. The smartphone 620 running the service application 130 (FIG. 1) displays the status of the connection on the smartphone's screen 1100. The parameters of the user are then obtained from the health application 110 (FIG. 1), displayed on the smartphone screen 1100, and recorded based on user preferences.

Figure 12:
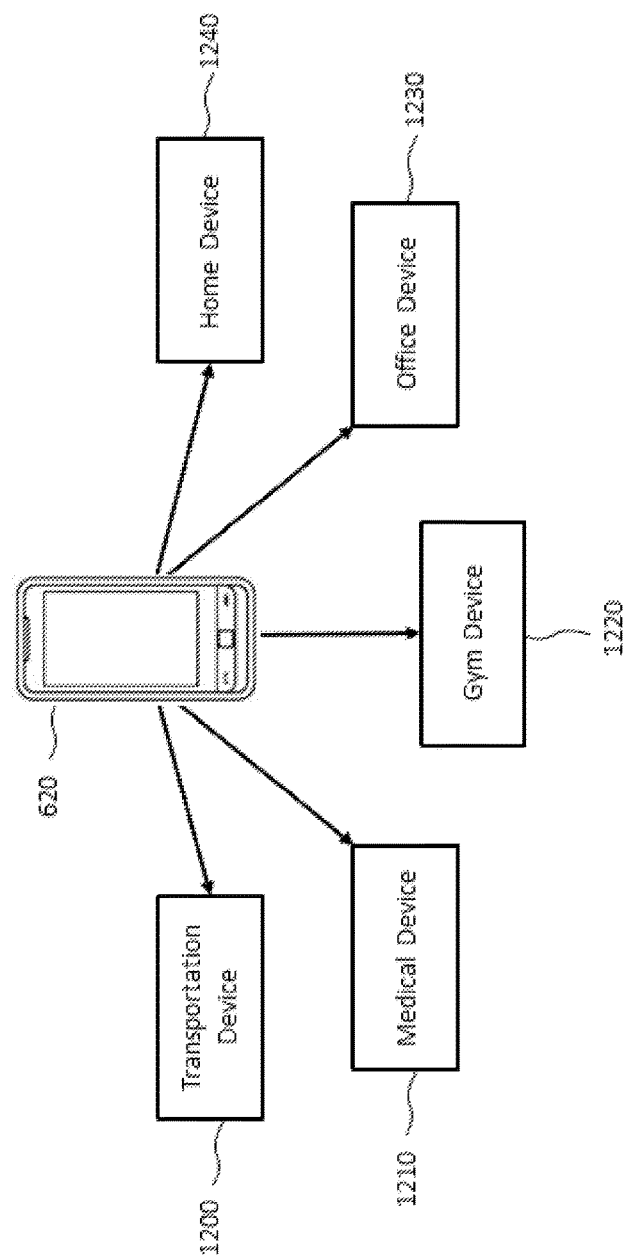
FIG. 12 is a diagram depicting a smartphone running the health application capable of collecting, storing, and transmitting data.

FIG. 12 illustrates an instance of the health application 110 (FIG. 1) running on a smartphone 620. The smartphone 620 is able to perform at least one of collect, store, transfer, process, and provide feedback through the health application 110 (FIG. 1). Data or processed information is received from any connected data generating device 420 (FIG. 4), with or without the presence of a connected server. The health application 110 (FIG. 1) is capable of modifying the data generating device 420 (FIG. 1) function (e.g. mode, weight, necessary repetitions, resistance, speed, etc.) or generating feedback (e.g. vibrations, sounds, lights, displays, etc.). Feedback can prompt, provide, network, and/or otherwise influence user interaction. Though depicted as a smartphone 620 within the figure, any device can run the health application 110 (FIG. 1). Data generating devices 420 (FIG. 4) that can connect to the health application 110 (FIG. 1) include: transportation device 1200, medical device 1210, gym device 1220, office device 1230, and home device 1240.

Figure 13:
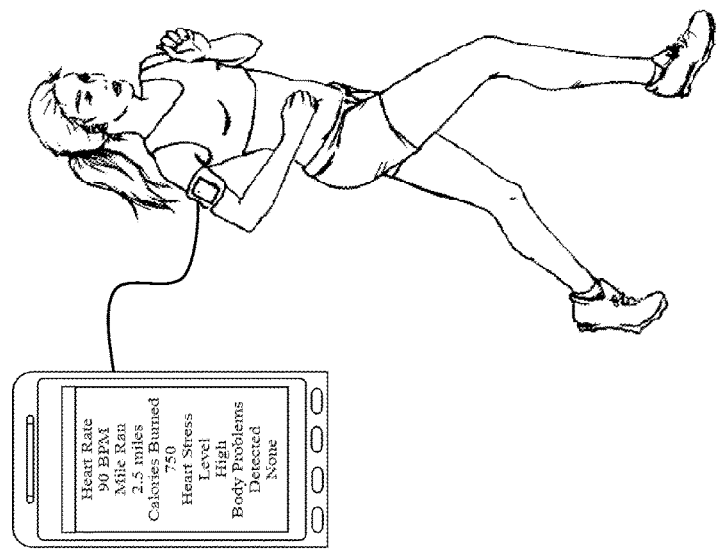
FIG. 13 illustrates the health application running on a portable device that is collecting data.

FIG. 13 illustrates a user collecting exercise data with a device 1300 running the health application 110 (FIG. 1). The device 1300 is securely connected to a data generating device 420 (FIG. 4) and the built in sensors located in the footwear 1320. The data generating device 420 (FIG. 4) can be one of contact and noncontact sensors. The device 1300 running the health application 110 (FIG. 1) is capable of constantly collecting health and fitness related data and storing the data based on user preferences. The collected data is also displayed on the device 1300 running the health application 110 (FIG. 1) to allow the user to see their current progress and any problems that may have been detected during exercise. The problems could be related to health or the equipment being used during exercise. The collected data may be displayed to the user on the device's 1300 user interface 1310.

Figure 14:
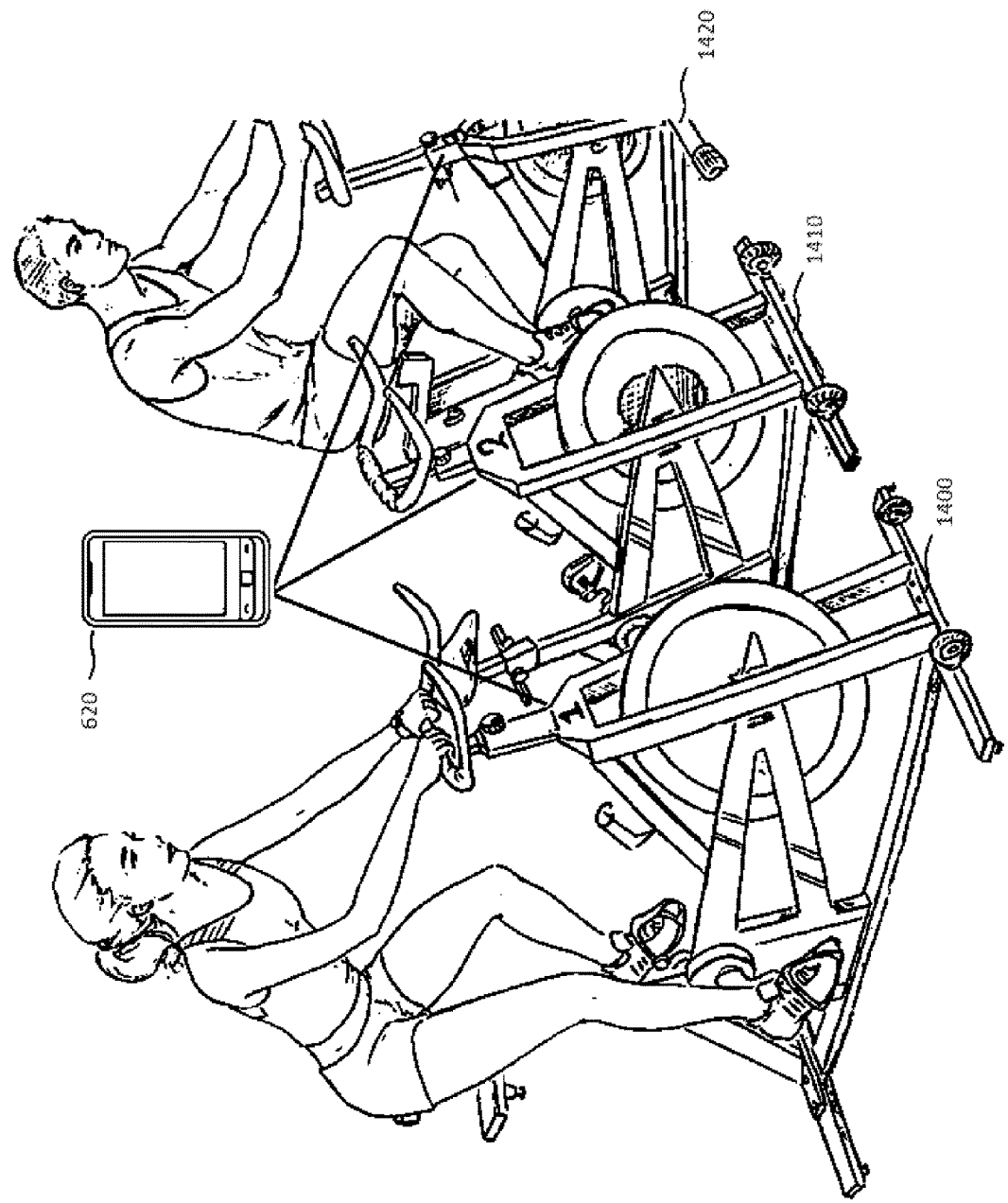
FIG. 14 illustrates the health application running on a smartphone that is collecting data at a gym.

FIG. 14 illustrates how the health application 110 (FIG. 1) can identify in-use health equipment 1400, 1420 and available health equipment 1410 in a gym. As the user enters the gym, the device running the health application 110 (FIG. 1) will connect to the local gym network. The local gym network can provide a list of authorized workout equipment. From this authorized workout list, the health application 110 (FIG. 1) will identify available equipment 1410 and/or notify the user when the equipment becomes available for use. The health application 110 (FIG. 1) running on the smartphone 620 can do one of selectively connect to available equipment 1410 and/or notify the user when the in-use equipment 1400, 1420 becomes available 1410.

Figure 15:
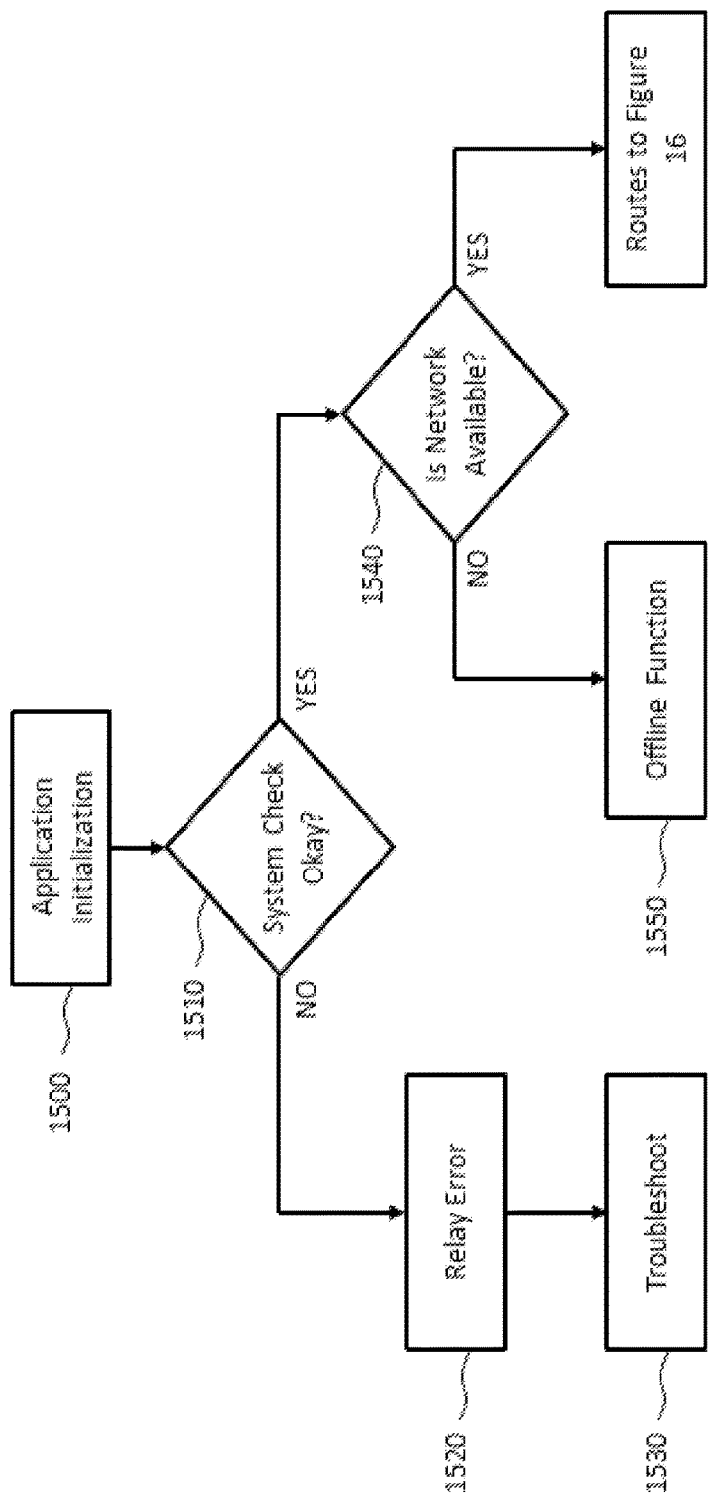
FIG. 15 is a flow diagram depicting a system check and troubleshooting routines of the initialization of an application.

FIG. 15 depicts how the health application 110 (FIG. 1) or the service application 130 (FIG. 1) goes through the initialization process 1500 which includes opening the application on one of personal computer 600 (FIG. 6), television 630 (FIG. 6), smartphone 620 (FIG. 6), or a stand-alone processor 610 (FIG. 6). A system check 1510 accesses one of stored or streamed data to determine if the application is malfunctioning. Failure to pass the system check, will cause the application to relay the error 1520 to at least one of the server 400 (FIG. 4) or the user. After an error is relayed, the health application 110 (FIG. 1) or service application 130 (FIG. 1) can attempt to resolve the error 1530 and prompt the user on failure. If no error exists, the application continues the initialization process by searching for a network 1540. This process can include connecting to one of cellular network, existing wireless network, and ad hoc network. If no network is found or established, operation is limited to offline functions 1550, including one of collecting, storing, processing, or recalling data or information stored on the device running the health application 110 (FIG. 1) or service application 130 (FIG. 1).

Figure 16:
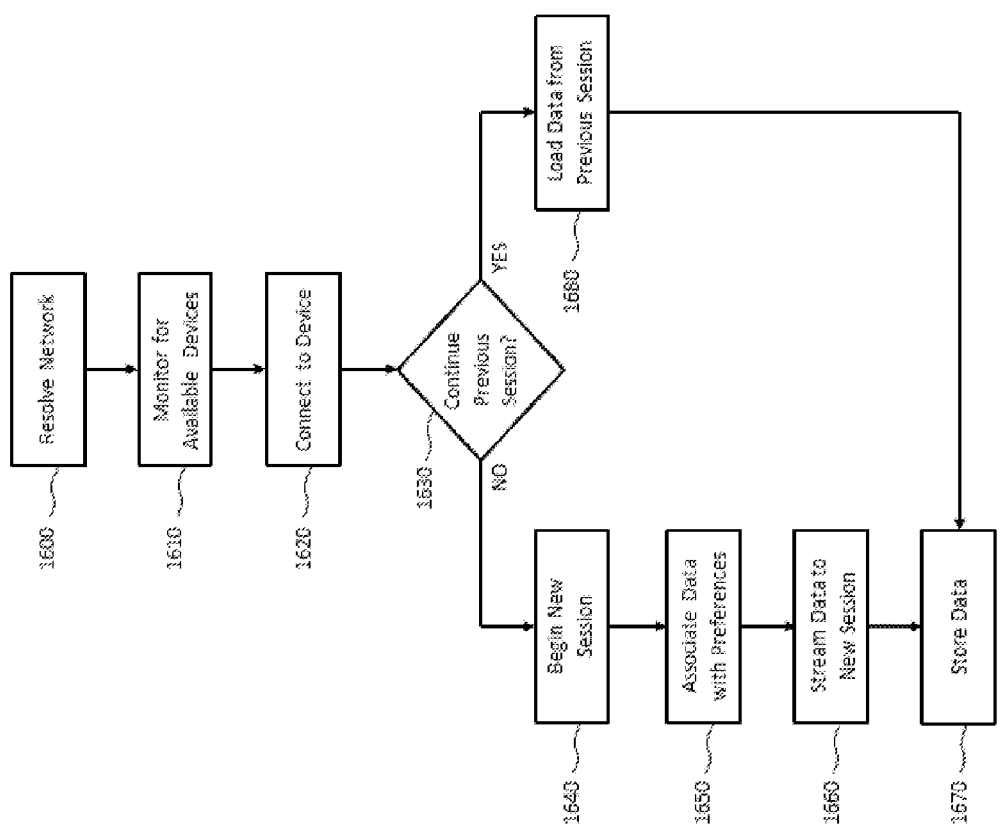
FIG. 16 is a flow diagram depicting the process of connecting a data source to the health application and collecting data.

FIG. 16 depicts a network resolution 1600 that includes one of the process of identifying, connecting, authorizing 1620, and any other steps that may be part of a selected network's initialization and connection process. Based on user preferences, the network will be resolved 1600 either automatically or after receiving manual user input. The network can consist of one of the server, local network, or offline network. Once selectively connected to a network, the health application 110 (FIG. 1) will monitor 1610 for available data generating devices 400 (FIG. 4). The health application 110 (FIG. 1) can selectively connect 1620 to one or more data generating devices 400 (FIG. 4) automatically or selected via user input. The health application 110 (FIG. 1) connects 1620 to the device by sending a request to the device and receiving confirmation that the device is connected. The connection is secured through a variety of protocols. Once connected, a new or continued data session 1630 can be prompted by the health application 110 (FIG. 1) by either opening a data session 1640 or recording the incoming data stream to an existing file 1680. This can occur automatically or manually. When a new session is selected, the data can be stored in memory 1670 on one of the device, cloud, or server. Beginning a new session 1640 can associate data with personal preferences 1650. New preferences can be created based on one of user input, advisory input, healthcare professional input, or based on repeated behavior and can be stored on one of the device, network, or server. The data streamed from the device will be recorded over the duration of the session. The health application 110 (FIG. 1) can stream data to new session 1660 and store data 1670 on one of a device, server, local network, or website. If user opts to continue from previous session, the health application 110 (FIG. 1) can load data from the previous session 1680 and new data can be added to the previous session. The data collected while on the offline network can be uploaded to one of the health monitoring system server 400 (FIG. 4), website, or personal computer when a connection is established and can be combined with previous data as determined by the user.

Figure 17:
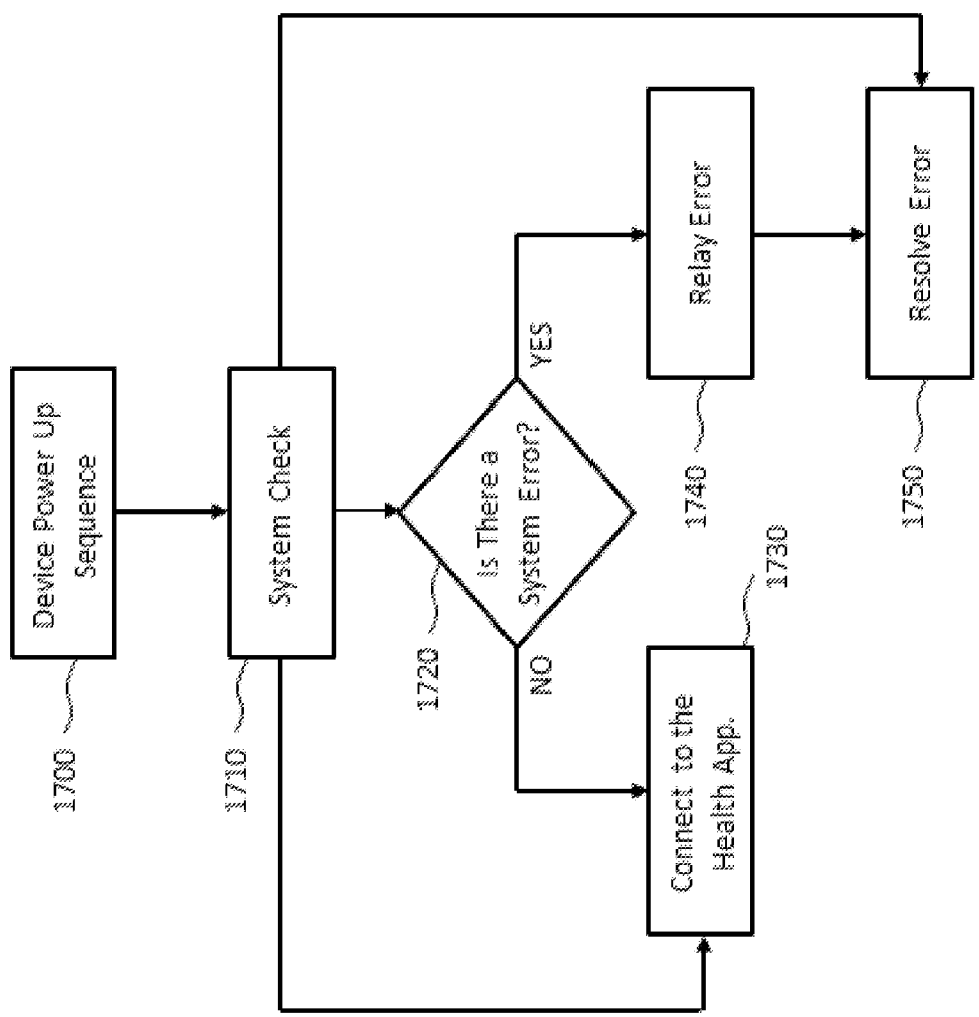
FIG. 17 is a flow diagram depicting system check and initialization of a data generating device.

FIG. 17 depicts how the data generating device 420 (FIG. 4) powers up 1700 and continuously monitors the data generating device 420 (FIG. 4) for error. The data generating device 420 (FIG. 4) will perform a system check 1710 to identify if any system errors have occurred 1720. If no system errors have occurred, the data generating device 420 (FIG. 4) can connect 1730 to the health application 110 (FIG. 1). If system errors have occurred, the data generating device will relay error 1740 to one of the user, health application 110 (FIG. 1), or server. The data generating device 420 (FIG. 4) will attempt to resolve error 1750.

Figure 18:
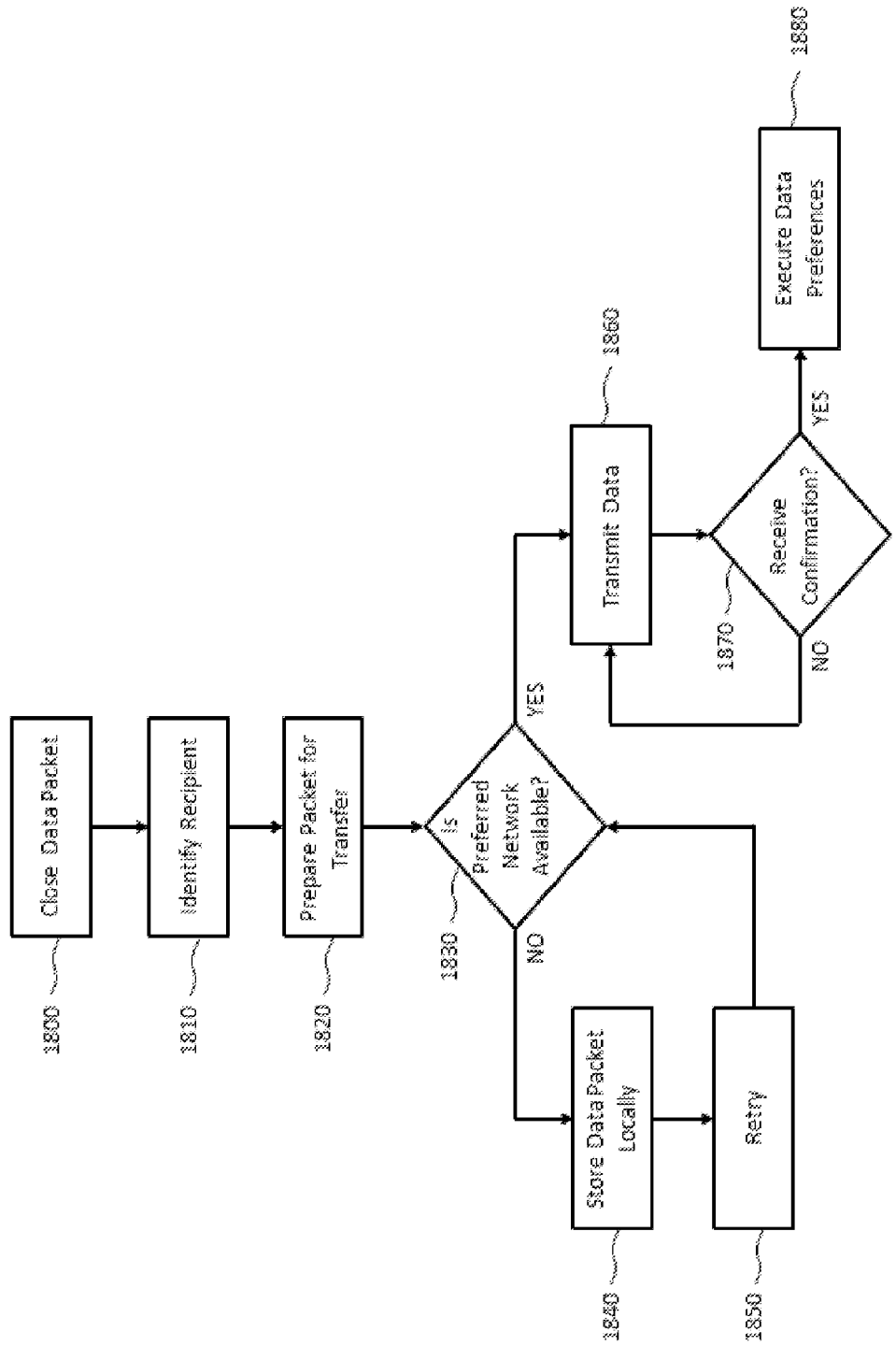
FIG. 18 is a flow diagram depicting how a data packet with routing information is transmitted to an application.

FIG. 18 depicts how data collected while on the offline network is transferred from the health application 110 (FIG. 1) to one or more of the server 400 (FIG. 4) local network, or website when a preferred connection is established. The health application 110 (FIG. 1) will close the data packet 1800, identify the recipient of the data packet 1810, and then prepare the packet for transfer 1820. When the preferred network is available 1830, the health application 110 (FIG. 1) will transmit data 1860 to one or more of the server 400

(FIG. 4), local network, or website. When the data has been received by one of the server 400 (FIG. 4), local network, or website, the health application 110 (FIG. 1) will receive confirmation 1870 that the data has been successfully transmitted. After the data is received, one of the server 400 (FIG. 4), local network, service application 130 (FIG. 1), or website will execute data preferences 1880. If no preferred network is available, the data packet will be stored locally 1840 on the device running the health application 110 (FIG. 1). The health application 110 (FIG. 1) can retry transmitting 1860 the assembled packet when the next preferred network is available. If a preferred network is available, the health application 110 (FIG. 1) will transmit data 1860 to one or more of the server 400 (FIG. 4), local network, or website.

Figure 19:
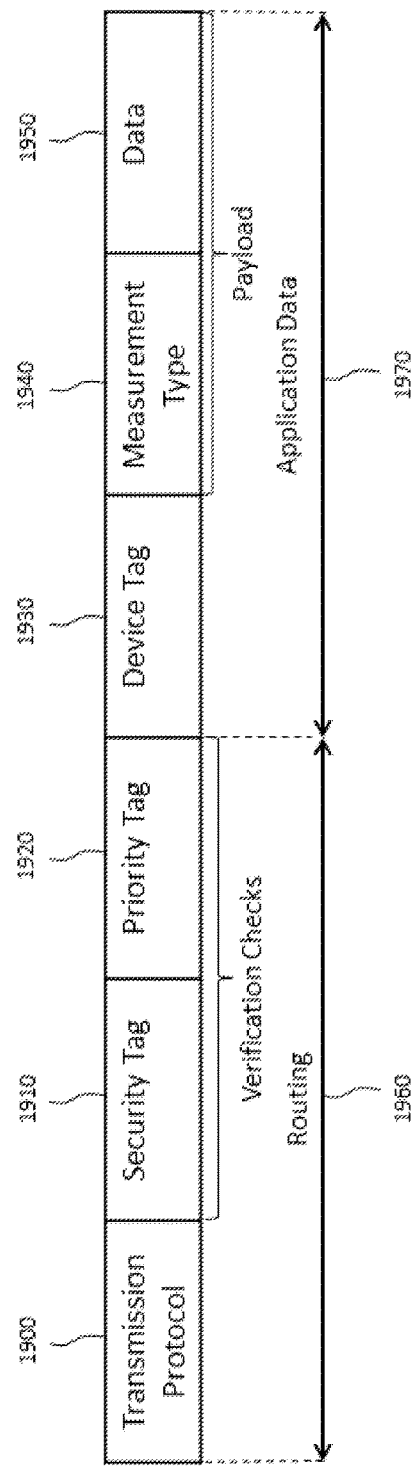
FIG. 19 is a block diagram depicting an example data packet.

FIG. 19 depicts elements of a transmission data packet. The diagram can include all components listed, but may vary according to the needs of connected applications and devices. When a device transmits a data packet, the routing 1960 portion will comprise at least one of the transmission protocol 1900, the security tag 1910, and the priority tag 1920. The transmission protocol 1900 can vary based on the network used to connect the devices to the health application 110 (FIG. 1). The security tag 1910 and the priority tag 1920 are detectable by any device, and can be modified based on the packet destination, or in the case of priority, different packet handling techniques. Error messages or emergency information can be decomposed and transmitted differently by the device running the health application 110 (FIG. 1) or a service application 130 (FIG. 1). The security tag 1920 will be used to prevent unauthorized access or use of the personal information including, but not limited to all of the application data 1970. Application data 1970 comprises the device tag 1930 and the payload, comprising of measurement type 1940 and the data 1950. The device tag 1930 identifies the device and allows connected applications to locate drivers or files pertinent to data 1950 interpretation and allocation.

Figure 20:
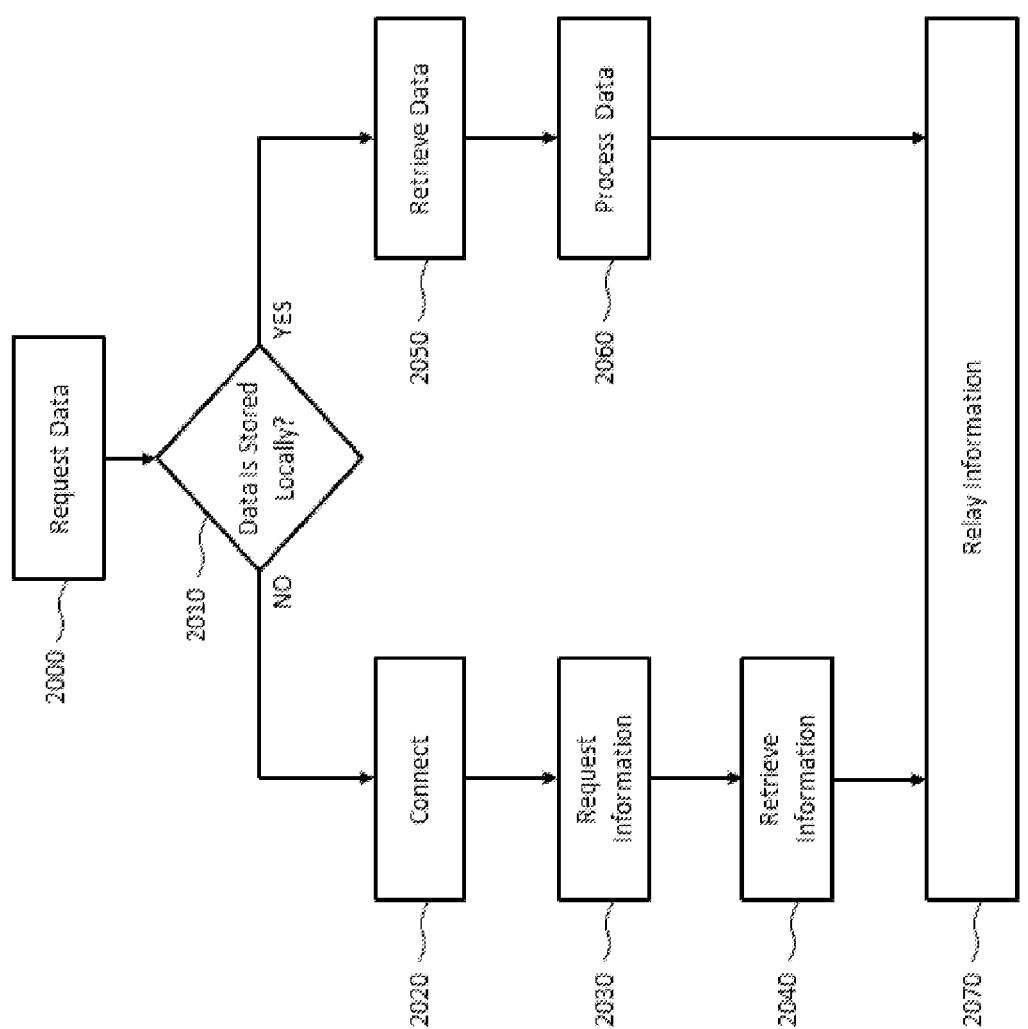
FIG. 20 is a flow diagram depicting how information is retrieved.

FIG. 20 depicts how the health application 110 (FIG. 1) can request data 2000 from one of a server 400 (FIG. 4), local network, website, or device. The requested data 2000 can comprise one or more of device drivers, past workouts, recommended workout, nutrition data, or medical data. The health application 110 (FIG. 1) or the service application 130 (FIG. 1) can request data automatically or by user selection. The health application 110 (FIG. 1) will determine if the data is stored locally 2010. If no data is stored locally, the health application 110 (FIG. 1) will connect 2020 to one or more of the server 400 (FIG. 4), local network, or website. The health application 110 (FIG. 1) will request information 2030 and retrieve information 2040 from one or more of the server 400 (FIG. 4), local network, or website. If the data is stored locally, the health application 110 (FIG. 1) will retrieve data 2050 from the device and process data 2060. When the requested information is retrieved from one of a server 400 (FIG. 4), local network, website, or device the health application 110 (FIG. 1) will relay information 2070 to the user.

Figure 21:
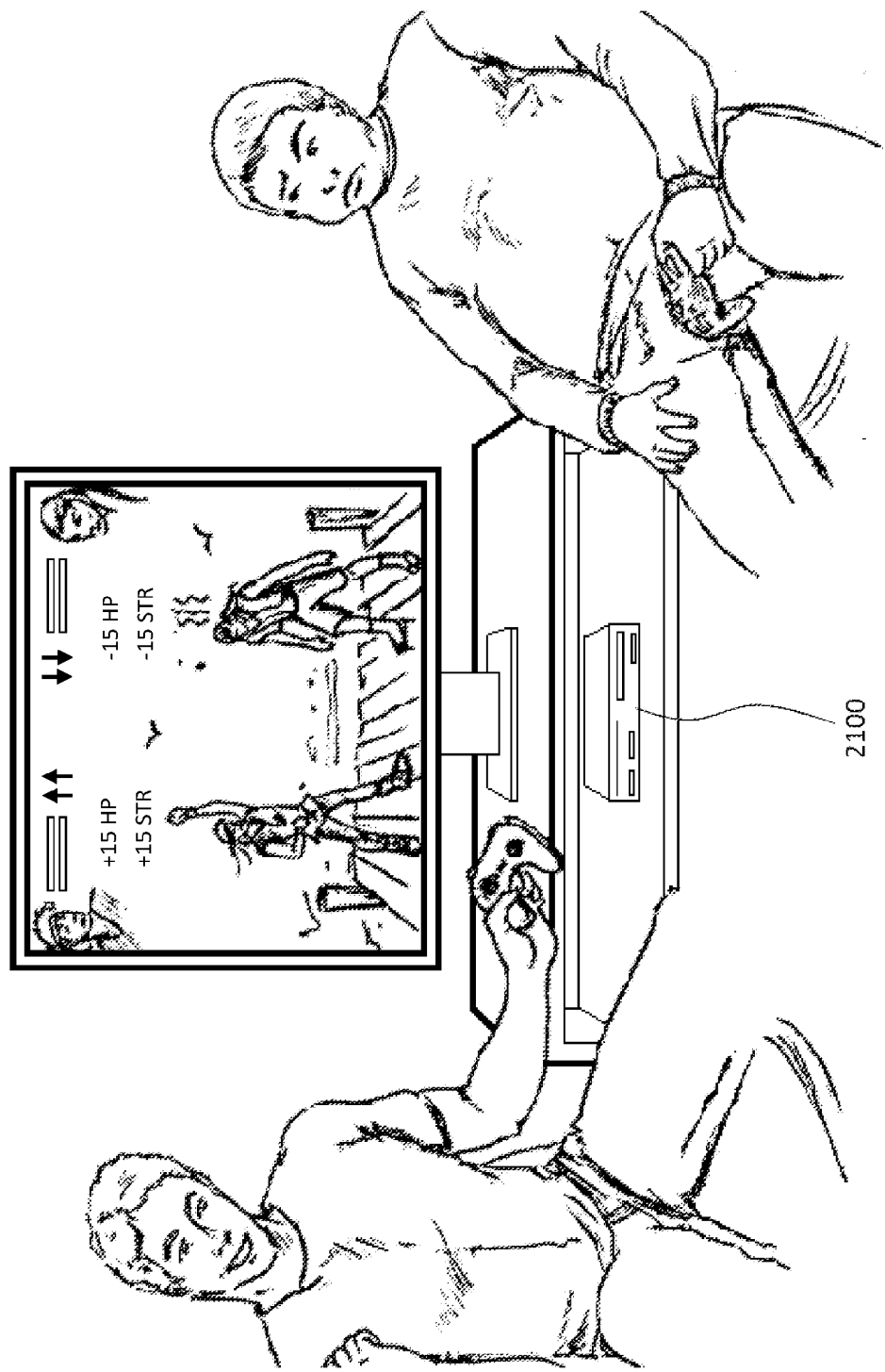
FIG. 21 illustrates how the user's progress can be incorporated into a game.

FIG. 21 illustrates two users having used the health application 110 (FIG. 1) to gather data which is used to reflect their personal fitness and health on their respective characters in a game 2100. This game 2100 is incorporated in the abilities of the invention with a purpose to encourage users to improve personal physical fitness and health. A user's game character may directly reflect the real world fitness and health status of the user. The game may comprise any format such as one-on-one physical combat as depicted, military combat and strategy, fantasy role-playing, or any other form in which points, traits, skills, and other attributes or accessories may be rewarded based on one of personal fitness, health, nutrition, and improvement thereof. The points, traits, skills, and other attributes or accessories earned may also be applied to existing games that choose to participate.

Figure 22:
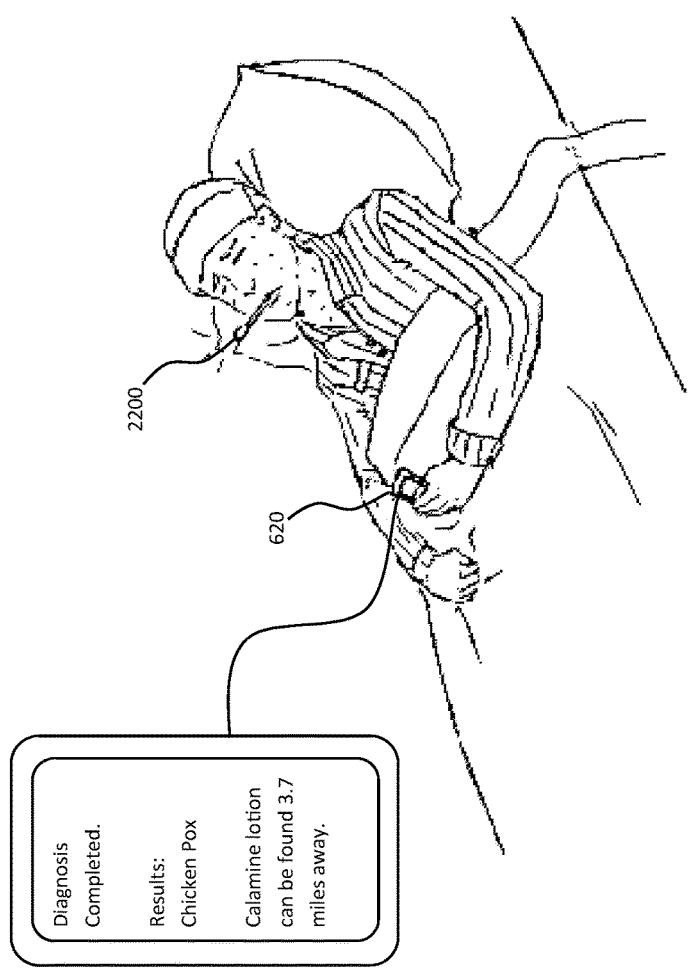
FIG. 22 illustrates the health application being used to diagnose illnesses and make recommendations.

FIG. 22 illustrates a user collecting data from a thermometer 2200 that is capable of generating data. The data is then sent to the health application 110 (FIG. 1) running on a smartphone 620. Additional symptom data may be submitted to the health application 110 (FIG. 1) manually by the user or gathered from other data generating devices 420 (FIG. 4). The health application 110 (FIG. 1) may display feedback to the user about their health or fitness state, and suggestions for the user to review based on the collected and/or manually entered data.

Figure 23:
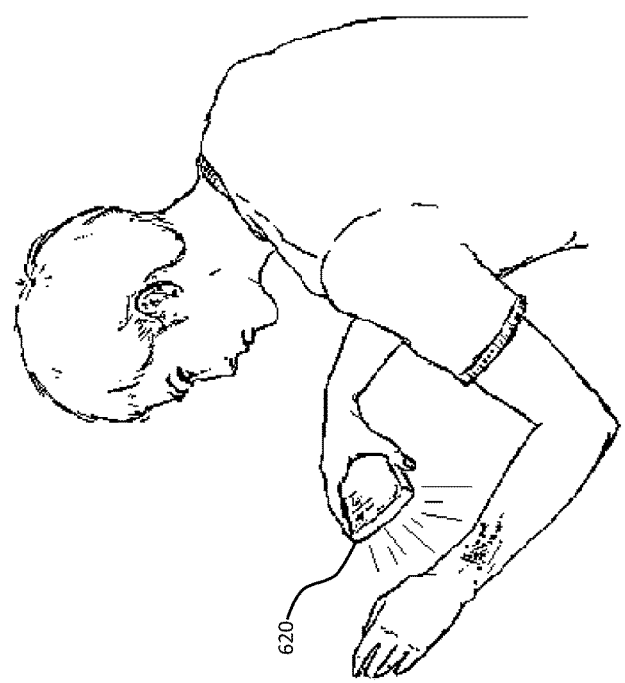
FIG. 23 illustrates the health application being used to diagnose a rash.

FIG. 23 illustrates a user using a smartphone 620 to capture a picture of a rash on his arm. This picture is then uploaded to a diagnosing website and/or a health professional for immediate and convenient diagnosis. Although the figure shows a user utilizing a smartphone 620 to capture a picture, other methods of receiving a diagnosis are available. These other methods include using other devices to automatically upload information that can be accessed by a health professional for monitoring. An example would be an insulin device tracking blood sugar levels and automatically transmitting and/or storing the data on a server, local network, or web site that is remotely monitored by a health professional. User preferences may be set to only send data to one or more specific health professionals, or to automatically connect to the first available health professional.

Figure 24:
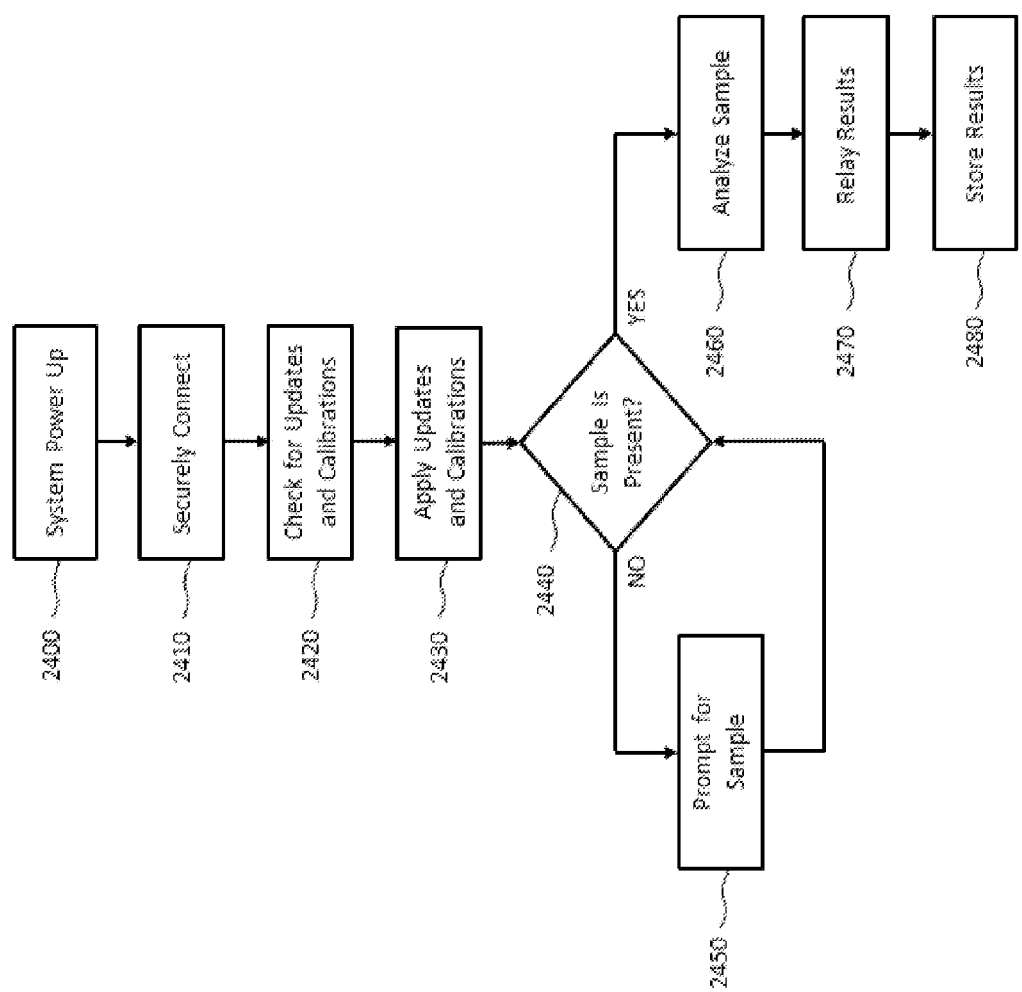
FIG. 24 is a flow diagram depicting a device capable of sampling and obtaining data from biological matter.

FIG. 24 depicts a data generating device 420 (FIG. 4) analyzing bio-material consisting of one of hair, blood, urine, stool and saliva. The data generating device 420 (FIG. 4) system power up 2400 sequence will be initiated by one of contact or noncontact. When the data generating device 420 (FIG. 4) is powered up 2400, the device can securely connect 2410 to the health application 110 (FIG. 1) if selected by the user. One of the data generating device 420 (FIG. 4), user, or the health application 110 (FIG. 1) will check for updates 2420 and calibrations located on one of a server 400 (FIG. 4), local network, website, or device. One of the data generating device 420 (FIG. 4), user, or the health application 110 (FIG. 1) will apply updates and calibrations 2430 to the data generating device 420 (FIG. 4). One of the data generating device 420 (FIG. 4), user, or the health application 110 (FIG. 1) will detect whether or not the biological sample is present 2440. If the biological sample is not present 2440, one of the health application 110 (FIG. 1), server 400 (FIG. 4), or data generating device 420 (FIG. 4) will prompt for a sample 2450. If the biological sample is present, one of the health application 110 (FIG. 4), server 400 (FIG. 4), or a data generating device 420 (FIG. 4) will analyze sample 2460. When the biological sample analysis 2460 is complete, one of the health application 110 (FIG. 1) or the data generating device 420 (FIG. 4) will relay results 2470 to at least one of the user, website, or health care provider and store results 2480.

Figure 25:
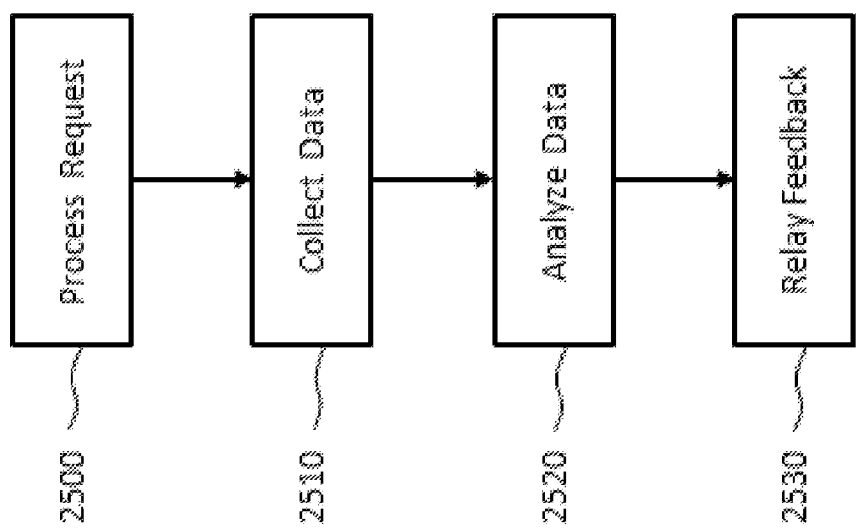
FIG. 25 depicts the process for obtaining feedback based on user specifications.

FIG. 25 depicts the process for requesting and obtaining feedback 2500 based on user specifications. The user requests health data using the health application 110 (FIG. 1) or the service application 130 (FIG. 1). The health data can be collected 2510 by one of health application 110 (FIG. 1), service application 130 (FIG. 1), and third party 200 (FIG. 2). Once the health data has been collected 2510, the health data is analyzed 2520 by one of the health application 110 (FIG. 1), service application 130 (FIG. 1), or third party 200

(FIG. 2). The health data is then relayed to the user 2530 through the health or service application 130 (FIG. 1).

Figure 26:
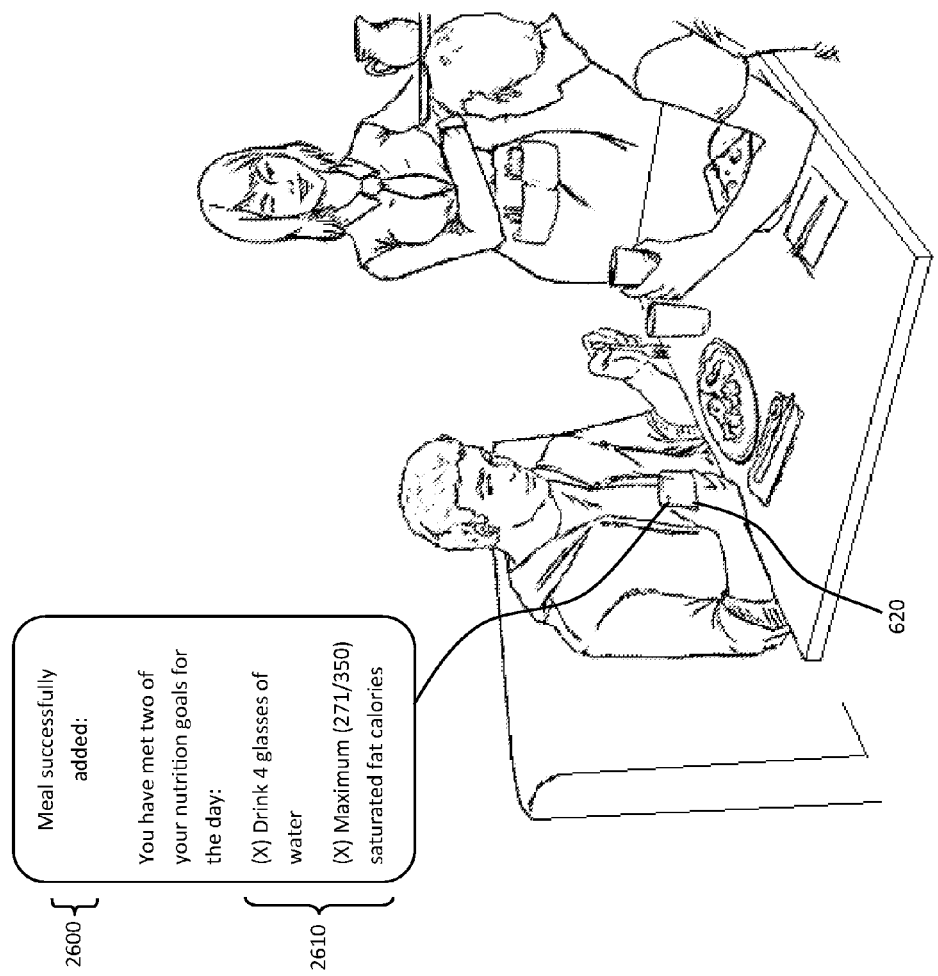
FIG. 26 illustrates a user receiving nutrition information about his meal in a restaurant.

FIG. 26 illustrates use of the nutrition functions of the device where a user is able to receive dietary information related to a meal. A restaurant might have meal information available online, on a device, or a running application designed to connect to the user's smartphone 620 running the health application 110 (FIG. 1) or the service application 130 (FIG. 1). Meal selection may be entered manually by the user or automatically by the device or server 400 (FIG. 4). The health application 110 (FIG. 1) or the service application 130 (FIG. 1) may make recommendations for restaurant and meal selections based on user criteria such as allergies, past workouts, or preferred diet. The health application 110 (FIG. 1) or the service application 130 (FIG. 1) is also capable of recommending activities to assist in meeting nutritional goals based on user criteria.

Figure 27:
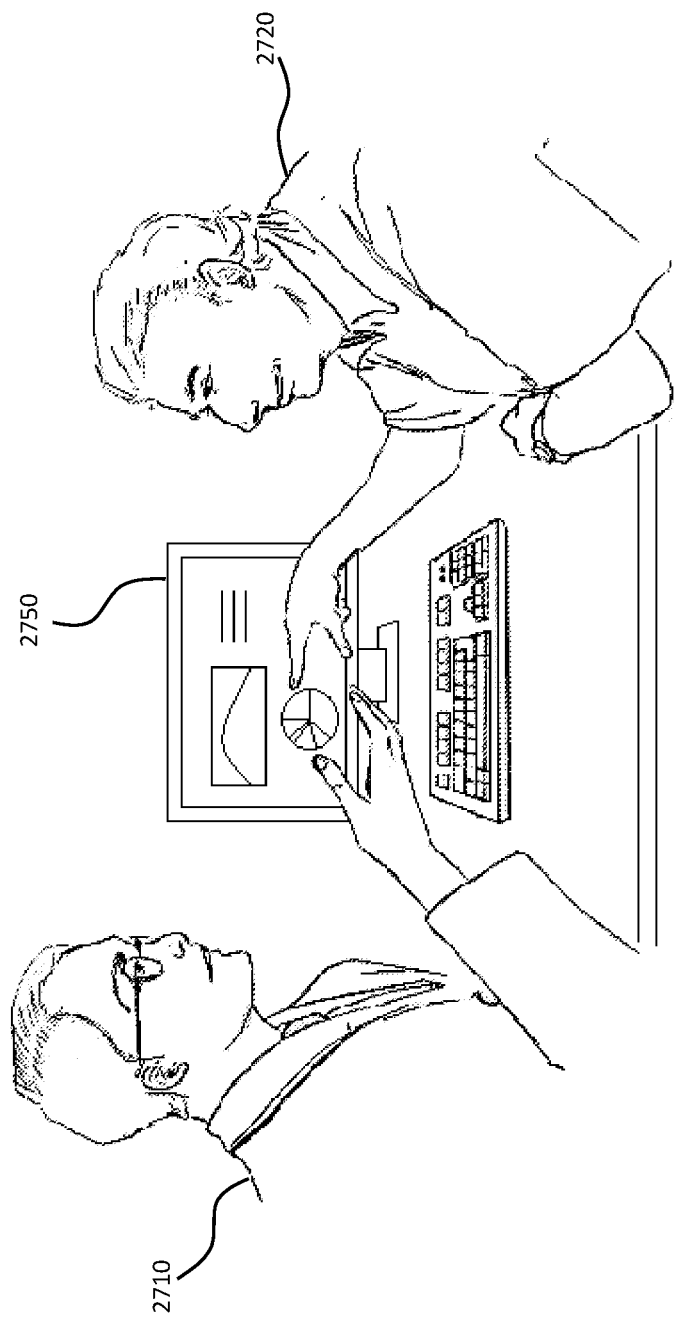
FIG. 27 illustrates a health professional reviewing health data with a patient.

FIG. 27 illustrates a user 2720 and health professional 2710 reviewing health data. The health application 110 (FIG. 1) or service application 130 (FIG. 1) is capable of presenting the health professional 2710 with selected information on a display 2750. The health care professional 2710 can be one of a medical professional, personal trainer, nutritionist or other professionals in health and/or fitness fields and the user's information is used to make accurate diagnosis and/or to help with recommendations. Though the illustration shows both the user and the professional 2710, the data may be reviewed independently by either party, allowing a user to track their own health and overall wellness or for the professional 2710 to make recommendations without the need of a face to face meeting.

Figure 28:
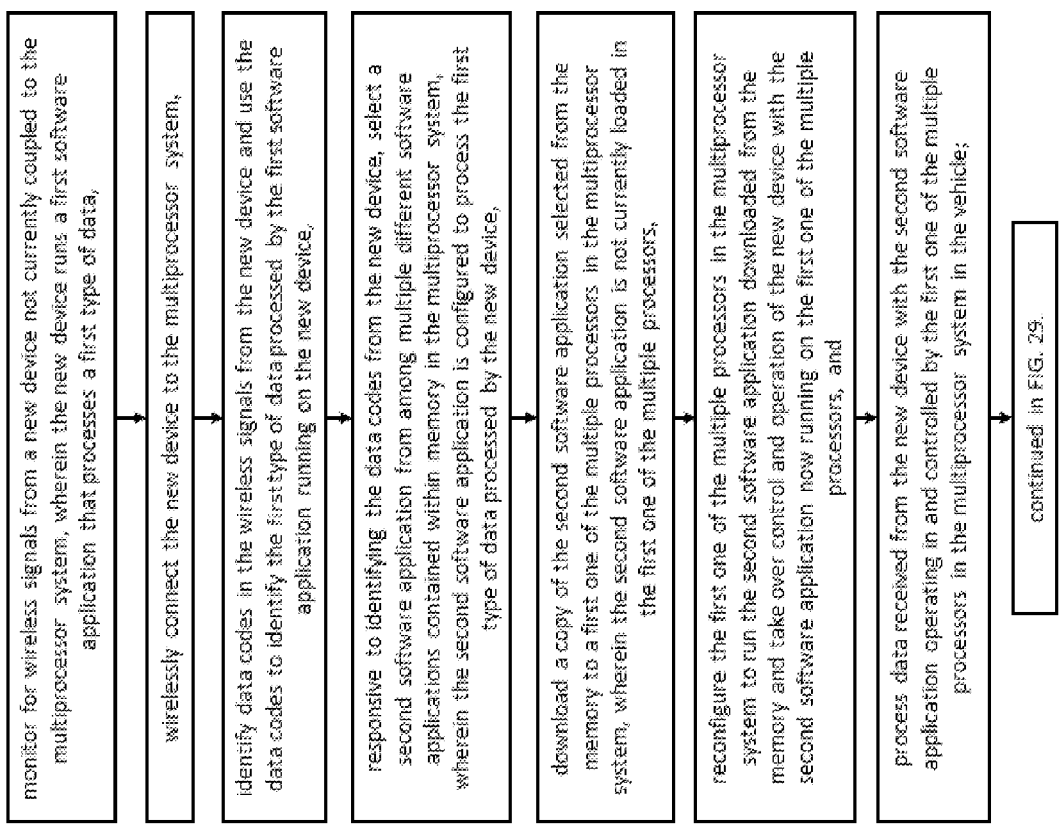
FIG. 28 is a flow diagram depicting process configuration.
Figure 29:
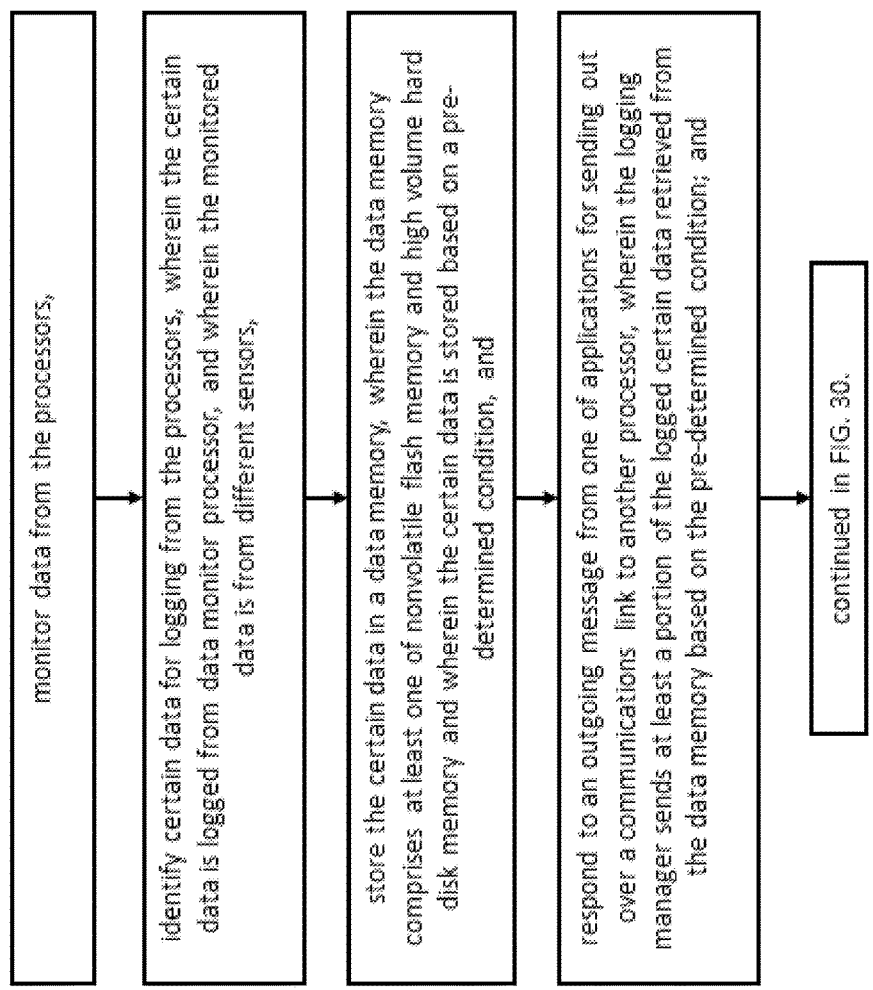
FIG. 29 is a flow diagram depicting operating a logging manager.
Figure 30:
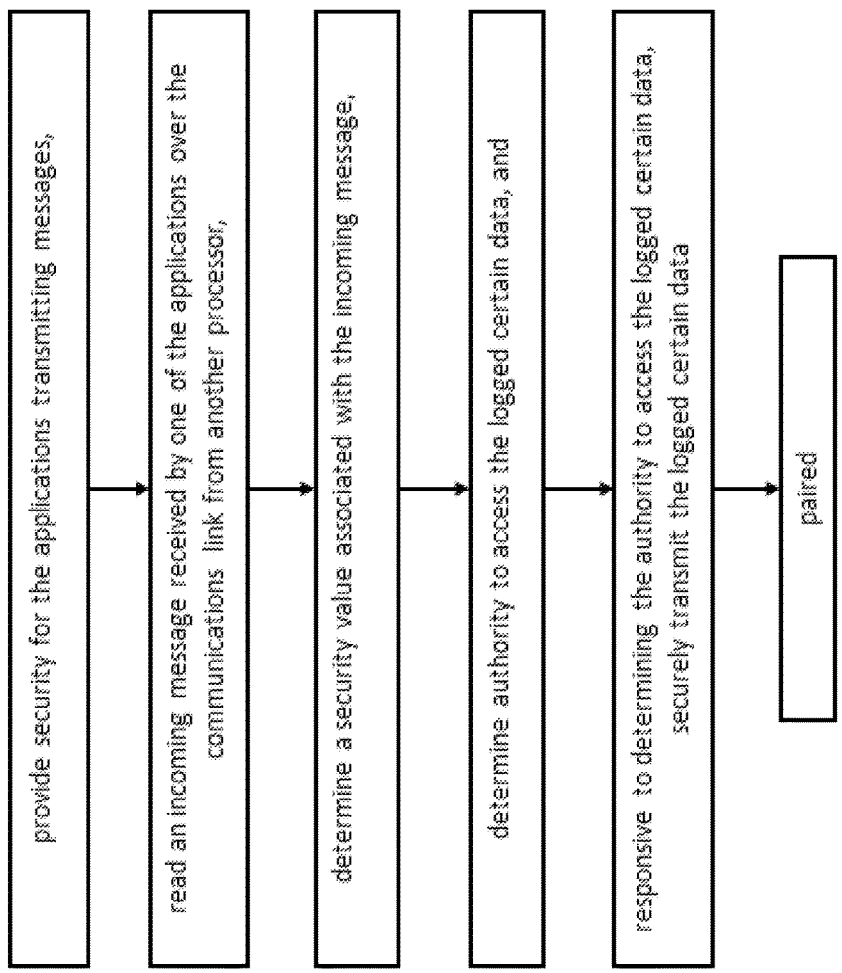
FIG. 30 is a flow diagram depicting operating a security manager.

FIGS. 28, 29 and 30 illustrate the process steps of Secure Simple Pairing including configuration management, data logging management and security management as disclosed in the U.S. Pat. No. 7,146,260 patent.

Non-Transitory Computer Readable Medium

Certain aspects of the present disclosure may also be embodied as computer readable code on a non-transitory computer readable recording medium. A non-transitory computer readable recording medium is any data storage device that can store data, which can be thereafter read by a computer system. Examples of the non-transitory computer readable recording medium include read only memory (ROM), random access memory (RAM), compact disc-ROMs (CD-ROMs), magnetic tapes, floppy disks, optical data storage devices, and carrier waves (such as data transmission through the Internet). The non-transitory computer readable recording medium can also be distributed over network coupled computer systems so that the computer readable code is stored and executed in a distributed fashion. In addition, functional programs, code, and code segments for accomplishing the present disclosure can be easily construed by programmers skilled in the art to which the present disclosure pertains.

It can be appreciated that a method and apparatus according to an embodiment of the present disclosure may be implemented by hardware, software and/or a combination thereof. The software may be stored in a non-volatile storage, for example, an erasable or re-writable ROM, a memory, for example, a RAM, a memory chip, a memory device, or a memory integrated circuit (IC), or an optically or magnetically recordable non-transitory machine-readable (e.g., computer-readable), storage medium (e.g., a CD, a digital versatile disk (DVD), a magnetic disk, a magnetic tape, and/or the like). A method and apparatus according to an embodiment of the present disclosure may be implemented by a computer or a mobile terminal that includes a controller and a memory, and the memory may be an example of a non-transitory machine-readable (e.g., computer-readable), storage medium suitable to store a program or programs including instructions for implementing various embodiments of the present disclosure.

The present disclosure may include a program including code for implementing the apparatus and method as defined by the appended claims, and a non-transitory machine-readable (e.g., computer-readable), storage medium storing the program. The program may be electronically transferred via any media, such as communication signals, which are transmitted through wired and/or wireless connections, and the present disclosure may include their equivalents.

An apparatus according to an embodiment of the present disclosure may receive the program from a program providing device which is connected to the apparatus via a wire or a wireless and store the program. The program providing device may include a memory for storing instructions which instruct to perform a content protect method which has been already installed, information used for the content protect method, and the like, a communication unit for performing a wired or a wireless communication with a graphic processing device, and a controller for transmitting a related program to a transmitting/receiving device based on a request of the graphic processing device or automatically transmitting the related program to the transmitting/receiving device.

While the present disclosure has been shown and described with reference to various embodiments thereof, it will be understood by those skilled in the art that various changes in form and details may be made therein without departing from the spirit and scope of the present disclosure as defined by the appended claims and their equivalents.

For the sake of convenience, the operations are described as various interconnected functional blocks or distinct software modules. This is not necessary, however, and there may be cases where these functional blocks or modules are equivalently aggregated into a single logic device, program or operation with unclear boundaries. In any event, the functional blocks and software modules or described features can be implemented by themselves, or in combination with other operations in either hardware or software.

Having described and illustrated the principles of the systems, methods, processes, and/or apparatuses disclosed herein in a preferred embodiment thereof, it should be apparent that the systems, methods, processes, and/or apparatuses may be modified in arrangement and detail without departing from such principles. Claim is made to all modifications and variation coming within the spirit and scope of the following claims.

The embodiments in which an exclusive property or privilege is claimed are defined as follows:

1. A system for aggregating health data, comprising:
   a processor configured to:
   detect the availability of a health data generating device,
   connect to the health data generating device,
   identify a health data generating device record from a plurality of different health device data generating device records previously identified and stored in memory, wherein the health data generating device record includes previously identified data codes from the health data generating device and from a service application running on the health data generating device,
   authenticate the health data generating device with an authorized health data generating device list, responsive to identifying the data codes and service application running in the health data generating device from the stored health data generating device record, download a copy of a health application selected from a location in memory, selectively connect the health data generating device to the health application, responsive to connecting the health data generating device, request data from the health data generating device, responsive to receiving the requested data, process the requested data with the health application.

2. The system of claim 1, wherein the system may include more than one health data generating device.

3. The system of claim 1, wherein the connection is at least one of wired and wireless.

4. The system of claim 1, wherein the health application is executed on one of a cellular or satellite packet data device with an integrated user interface.

5. The system of claim 1, wherein the processor running the service application is capable of running the health application when collecting data from a health data generating device.

6. The system of claim 1, wherein the health data generating device comprises at least one of contact and noncontact sensors, wherein the noncontact sensors include image and infrared and contact sensors include temperature, oxygen levels, heart rate, and heart performance.

7. The system of claim 1, wherein the health data generating device generates data from an analytical instrument, wherein the analytical instrument analyzes bio material.

8. The system of claim 7, wherein the bio material include at least one of hair, blood, urine, stool, and saliva.

9. The system of claim 1, wherein data is stored within at least one of the health application, service application, and a server.

10. The system of claim 1, wherein responsive to processing the data the processor is further configured to generate a notification based on the data.

11. A method for aggregating health data, comprising:
configuring a processor to:
detect the availability of a health data generating device,
connect to the health data generating device,
identify a health data generating device record from a plurality of different health device data generating device records previously identified and stored in memory wherein the health data generating device record includes previously identified data codes from the health data generating device and from a service application running on the health data generating device,
authenticate the health data generating device with an authorized health data generating device list,
responsive to identifying the data codes and service application running in the health data generating device from the stored health data generating device record, download a copy of a health application selected from a location in memory,
selectively connect the health data generating device to the health application,
responsive to connecting the health data generating device, request data from the health data generating device,
responsive to receiving the requested data, process the requested data with the health application.

12. The method of claim 11, wherein the system may include more than one health data generating device.

13. The method of claim 11, wherein the connection is at least one of wired and wireless.

14. The method of claim 11, wherein the health application is executed on one of a cellular or satellite packet data device with an integrated user interface.

15. The method of claim 11, wherein the processor running the service application is capable of running the health application when collecting data from a health data generating device.

16. The method of claim 11, wherein the health data generating device comprises at least one of contact and noncontact sensors, wherein the noncontact sensors include image and infrared and contact sensors include temperature, oxygen levels, heart rate, and heart performance.

17. The method of claim 11, wherein the health data generating device generates data from an analytical instrument, wherein the analytical instrument analyzes bio material.

18. The method of claim 17, wherein the bio material include at least one of hair, blood, urine, stool, and saliva.

19. The method of claim 11, wherein data is stored within at least one of the health application, service application, and a server.

20. The method of claim 11, wherein responsive to processing the data the processor is further configured to generate a notification based on the data.

* * * * *